(12) United States Patent
Appel et al.

(10) Patent No.: US 7,887,844 B2
(45) Date of Patent: *Feb. 15, 2011

(54) MULTIPARTICULATE CRYSTALLINE DRUG COMPOSITIONS HAVING CONTROLLED RELEASE PROFILES

(75) Inventors: Leah E. Appel, Bend, OR (US); Roderick J. Ray, Bend, OR (US); David K. Lyon, Bend, OR (US); James B. West, Bend, OR (US); Scott B. McCray, Bend, OR (US); Marshall D. Crew, Bend, OR (US); Dwayne T. Friesen, Bend, OR (US); Scott M. Herbig, East Lyme, CT (US); Julian B. Lo, Old Lyme, CT (US)

(73) Assignee: Pfizer Inc., New York, NY (US)

( * ) Notice: Subject to any disclaimer, the term of this patent is extended or adjusted under 35 U.S.C. 154(b) by 1357 days.

This patent is subject to a terminal disclaimer.

(21) Appl. No.: 11/004,168

(22) Filed: Dec. 3, 2004

(65) Prior Publication Data

US 2005/0181062 A1    Aug. 18, 2005

Related U.S. Application Data

(60) Provisional application No. 60/527,329, filed on Dec. 4, 2003.

(51) Int. Cl.
*A61K 9/14* (2006.01)
*A61K 9/16* (2006.01)

(52) U.S. Cl. ...................... 424/489; 424/490

(58) Field of Classification Search .................. None
See application file for complete search history.

(56) References Cited

U.S. PATENT DOCUMENTS

| | | | |
|---|---|---|---|
| 2,955,956 A | 10/1960 | Baugh et al. | 117/100 |
| 4,053,264 A | 10/1977 | King | 425/8 |
| 4,086,346 A | 4/1978 | Bocker et al. | 424/253 |
| 4,092,089 A | 5/1978 | Bocker et al. | 425/10 |
| 4,293,570 A | 10/1981 | Vadasz | 426/3 |
| 4,474,768 A | 10/1984 | Bright | 424/180 |
| 4,517,359 A | 5/1985 | Kobrehel et al. | 536/7.4 |
| 4,675,140 A | 6/1987 | Sparks et al. | 264/4.3 |
| 4,874,611 A | 10/1989 | Wilson et al. | 424/410 |
| 4,931,285 A | 6/1990 | Edgren et al. | 424/473 |
| 4,957,681 A | 9/1990 | Klimesch et al. | 264/211.23 |
| 4,963,531 A | 10/1990 | Remington et al. | 514/29 |
| 5,019,302 A | 5/1991 | Sparks et al. | 264/8 |
| 5,024,842 A | 6/1991 | Edgren et al. | 424/473 |
| 5,047,244 A | 9/1991 | Sanvordeker et al. | 424/435 |
| 5,064,650 A | 11/1991 | Lew | 424/435 |
| 5,084,287 A | 1/1992 | Ghebre-Sellassie et al. | 424/495 |
| 5,100,592 A | 3/1992 | Sparks et al. | 264/7 |
| 5,143,662 A | 9/1992 | Chesterfield et al. | 264/8 |
| 5,160,743 A | 11/1992 | Edgren et al. | 424/473 |
| 5,169,645 A | 12/1992 | Shukla et al. | 424/499 |
| 5,183,690 A | 2/1993 | Carr et al. | 427/213.31 |
| 5,194,262 A | 3/1993 | Goldberg et al. | 424/401 |
| 5,196,199 A | 3/1993 | Fuisz | 424/401 |
| 5,213,810 A | 5/1993 | Steber | 424/490 |
| 5,236,734 A | 8/1993 | Fuisz | 426/641 |
| 5,292,657 A | 3/1994 | Rutherford et al. | 435/243 |
| 5,348,758 A | 9/1994 | Fuisz et al. | 426/660 |
| 5,380,473 A | 1/1995 | Bogue et al. | 264/11 |
| 5,405,617 A | 4/1995 | Gowan, Jr. et al. | 424/464 |
| 5,407,676 A | 4/1995 | Fuisz | 424/401 |
| 5,429,836 A | 7/1995 | Fuisz | 426/601 |
| 5,433,951 A | 7/1995 | Serajuddin et al. | 424/486 |
| 5,456,932 A | 10/1995 | Fuisz et al. | 426/548 |
| 5,461,089 A | 10/1995 | Handyside et al. | 523/171 |
| 5,500,162 A | 3/1996 | Theisen et al. | 264/9 |
| 5,501,858 A | 3/1996 | Fuisz | 424/439 |
| 5,505,983 A | 4/1996 | Kamada | 427/2.21 |
| 5,518,730 A | 5/1996 | Fuisz | 424/426 |
| 5,539,000 A | 7/1996 | Leonard | 514/682 |
| 5,549,917 A | 8/1996 | Cherukuri et al. | 426/96 |
| 5,556,652 A | 9/1996 | Cherukari et al. | 426/5 |
| 5,569,467 A | 10/1996 | Ruiz | 424/489 |
| 5,582,855 A | 12/1996 | Cherukuri | 426/5 |

(Continued)

FOREIGN PATENT DOCUMENTS

EP    0080341    6/1983

(Continued)

OTHER PUBLICATIONS

Savolainen, Marja et al., International Journal of Pharmaceutics, Aug. 27, 2003, vol. 262, No. 1-2., pp. 47-62, "Evaluation of polar lipid-hydrophilic polymer microparticles."

(Continued)

*Primary Examiner*—S. Tran
(74) *Attorney, Agent, or Firm*—Jennifer A. Kispert; Richard V. Zanzalari (57) ABSTRACT

A multiparticulate for controlled release of a drug comprises crystalline drug, a glyceride having at least one alkylate substituent of at least 16 carbon atoms, and a poloxamer, wherein at least 70 wt % of the drug in the multiparticulate is crystalline.

15 Claims, 3 Drawing Sheets

U.S. PATENT DOCUMENTS

| | | | |
|---|---|---|---|
| 5,597,416 A | 1/1997 | Fuisz et al. | 127/30 |
| 5,597,844 A | 1/1997 | Chauhan et al. | 514/400 |
| 5,601,761 A | 2/1997 | Hoffman et al. | 264/4.3 |
| 5,605,889 A | 2/1997 | Curatolo et al. | 514/29 |
| 5,633,006 A | 5/1997 | Catania et al. | 424/441 |
| 5,683,720 A | 11/1997 | Myers et al. | 424/489 |
| 5,690,959 A | 11/1997 | Palepu et al. | 424/472 |
| 5,705,190 A | 1/1998 | Broad et al. | 424/465 |
| 5,707,646 A | 1/1998 | Yajima et al. | 424/439 |
| 5,733,577 A | 3/1998 | Myers et al. | 424/488 |
| 5,741,519 A | 4/1998 | Rosenberg et al. | 424/464 |
| 5,744,180 A | 4/1998 | Cherukuri et al. | 426/99 |
| 5,747,058 A | 5/1998 | Tipton et al. | 424/423 |
| 5,766,521 A | 6/1998 | Le Thiesse et al. | 264/7 |
| 5,792,474 A | 8/1998 | Rauchfuss | 424/489 |
| 5,824,342 A | 10/1998 | Cherukuri et al. | 424/484 |
| 5,840,334 A | 11/1998 | Raiden et al. | 424/464 |
| 5,849,223 A | 12/1998 | Myers et al. | 264/15 |
| 5,851,553 A | 12/1998 | Myers et al. | 424/488 |
| 5,851,555 A | 12/1998 | Sanghvi et al. | 424/464 |
| 5,855,915 A | 1/1999 | Pinkus | 242/486 |
| 5,869,098 A | 2/1999 | Misra et al. | 424/484 |
| 5,869,101 A | 2/1999 | Moller et al. | 424/489 |
| 5,883,103 A | 3/1999 | Burnside et al. | 514/262 |
| 5,891,845 A | 4/1999 | Myers | 514/11 |
| 5,912,030 A | 6/1999 | Huzinec et al. | 426/3 |
| 5,919,489 A | 7/1999 | Saleki-Gerhardt et al. | 424/501 |
| 5,935,600 A | 8/1999 | Cherukuri et al. | 424/464 |
| 5,948,407 A | 9/1999 | McGuinness et al. | 424/184.1 |
| 5,952,004 A | 9/1999 | Rudnic et al. | 424/455 |
| 5,958,452 A | 9/1999 | Oshlack et al. | 424/457 |
| 5,965,161 A | 10/1999 | Oshlack et al. | 424/457 |
| 5,965,164 A | 10/1999 | Fuisz et al. | 424/489 |
| 5,972,373 A | 10/1999 | Yajima et al. | 424/439 |
| 5,980,941 A | 11/1999 | Raiden et al. | 424/464 |
| 6,010,718 A | 1/2000 | Al-Razzak et al. | 424/464 |
| 6,013,280 A | 1/2000 | Frisbee et al. | 424/464 |
| 6,048,541 A | 4/2000 | Mirsa et al. | 424/401 |
| 6,051,253 A | 4/2000 | Zettler et al. | 424/465 |
| 6,068,859 A * | 5/2000 | Curatolo et al. | 424/490 |
| 6,077,541 A | 6/2000 | Chen et al. | 424/480 |
| 6,083,430 A | 7/2000 | Fuisz et al. | 264/5 |
| 6,086,920 A | 7/2000 | Frisbee et al. | 424/489 |
| 6,090,830 A | 7/2000 | Myers et al. | 514/356 |
| 6,103,264 A | 8/2000 | Hoffmann et al. | 424/468 |
| 6,117,452 A | 9/2000 | Ahlgren et al. | 424/468 |
| 6,139,872 A | 10/2000 | Walsh | 424/464 |
| 6,165,512 A | 12/2000 | Mezaache et al. | 424/489 |
| 6,221,368 B1 | 4/2001 | Breitenbach et al. | 424/400 |
| 6,245,903 B1 | 6/2001 | Karimian et al. | 536/7.4 |
| 6,248,363 B1 | 6/2001 | Patel et al. | 424/497 |
| 6,261,599 B1 | 7/2001 | Oshlack et al. | 424/457 |
| 6,268,489 B1 | 7/2001 | Allen et al. | 536/7.4 |
| 6,270,804 B1 | 8/2001 | Getz et al. | 424/490 |
| 6,328,993 B1 | 12/2001 | Linder et al. | 424/451 |
| 6,335,033 B2 | 1/2002 | Oshlack et al. | 424/457 |
| 6,365,574 B2 | 4/2002 | Singer et al. | 514/29 |
| 6,383,510 B1 | 5/2002 | Linder et al. | 424/436 |
| 6,395,300 B1 | 5/2002 | Straub et al. | 424/489 |
| 6,423,345 B2 | 7/2002 | Bernstein et al. | 424/501 |
| 6,500,459 B1 | 12/2002 | Chhabra et al. | 424/474 |
| 6,551,616 B1 | 4/2003 | Notario et al. | 424/464 |
| 6,569,463 B2 | 5/2003 | Patel et al. | 424/497 |
| 6,576,258 B1 | 6/2003 | Kofler et al. | 424/458 |
| 6,645,528 B1 | 11/2003 | Straub et al. | 424/489 |
| 6,682,759 B2 | 1/2004 | Lim et al. | 424/468 |
| 6,689,390 B2 | 2/2004 | Bernstein et al. | 424/501 |
| 6,692,767 B2 | 2/2004 | Burnside et al. | 424/489 |
| 6,984,403 B2 * | 1/2006 | Hagen et al. | 424/489 |
| 2001/0003590 A1 | 6/2001 | Joachim et al. | 424/465 |
| 2001/0006650 A1 | 7/2001 | Burnside et al. | 424/400 |
| 2002/0009433 A1 | 1/2002 | Curatolo et al. | 424/94.1 |
| 2002/0025342 A1 | 2/2002 | Linder et al. | 424/489 |
| 2002/0032171 A1 | 3/2002 | Patel et al. | |
| 2002/0044968 A1 | 4/2002 | Van Lengerich | 424/469 |
| 2003/0003064 A1 * | 1/2003 | Kalla et al. | 424/63 |
| 2003/0104063 A1 * | 6/2003 | Babcock et al. | 424/486 |
| 2003/0165563 A1 | 9/2003 | Murphy et al. | 424/465 |
| 2003/0180352 A1 | 9/2003 | Patel et al. | 424/465 |
| 2003/0190365 A1 | 10/2003 | Fergione et al. | 424/489 |
| 2003/0228357 A1 | 12/2003 | Johnson et al. | 424/465 |
| 2004/0014951 A1 | 1/2004 | Dumic et al. | 536/7.1 |
| 2004/0121003 A1 | 6/2004 | Chickering, III et al. | 424/465 |
| 2005/0026851 A1 | 2/2005 | Danilovski et al. | 514/28 |

FOREIGN PATENT DOCUMENTS

| | | |
|---|---|---|
| EP | 0109253 | 5/1984 |
| EP | 0582396 | 2/1994 |
| EP | 0925789 | 6/1999 |
| EP | 0943341 | 9/1999 |
| EP | 1127580 | 8/2001 |
| EP | 1227102 A1 * | 7/2002 |
| GB | 2066070 | 7/1981 |
| GB | 2091097 | 7/1982 |
| IN | 187487 | 5/2000 |
| WO | WO 9107171 | 5/1991 |
| WO | WO 9400112 | 1/1994 |
| WO | WO 9427557 | 12/1994 |
| WO | WO 9509601 | 4/1995 |
| WO | WO 9806714 | 2/1998 |
| WO | WO 9818610 | 5/1998 |
| WO | WO 9846239 | 10/1998 |
| WO | WO 9856357 | 12/1998 |
| WO | WO 9903453 | 1/1999 |
| WO | WO 9924031 | 5/1999 |
| WO | WO 0026285 | 5/2000 |
| WO | 0057886 | 10/2000 |
| WO | WO 0142221 | 6/2001 |
| WO | WO 0178688 | 10/2001 |
| WO | WO 0185135 | 11/2001 |
| WO | WO 0224174 | 3/2002 |
| WO | WO 02064121 | 8/2002 |
| WO | WO 03018031 | 3/2003 |
| WO | WO 03032922 | 4/2003 |
| WO | WO 03037304 | 5/2003 |
| WO | WO 03035402 | 7/2003 |
| WO | WO 03063832 | 8/2003 |
| WO | WO 03063833 | 8/2003 |
| WO | WO 03063834 | 8/2003 |
| WO | WO 03068191 | 8/2003 |
| WO | WO 03105810 | 12/2003 |
| WO | WO 04000865 | 12/2003 |
| WO | WO 2004009608 | 1/2004 |
| WO | WO 2004035063 | 4/2004 |
| WO | WO 2004087096 | 10/2004 |

OTHER PUBLICATIONS

Curatolo, et al., US Patent Application Publication No. US 2002/0009433, U.S. Appl. No. 09/788,886, Published Jan. 24, 2002.

Dunne, U.S. Patent Application Publication No. US 2004/0023898, U.S. Appl. No. 10/628,102, Published Feb. 5, 2004.

Foulds, G., et al., "The effects of an antacid or cimetidine on the serum concentrations of azithromycin", J. Clin. Pharmacol. Feb. 1991; 31(2): 164-7 (Abstract).

Amsden, G.W., et al., "Serum and WBC pharmacokinetics of 1500 mg of azithromycin when given either as a single dose or over a 3 day period in healthy volunteers", J. Antimicrobial Chemotherapy (2001), 47(1), 61-66 (Abstract).

Barber, J., "Assignments of the $^{13}$C and $_1$H NMR Spectra of Azithromycin in CDCI$_3$," *Magnetic Resonance in Chemistry* 29:7(1991)740-743.

Barthelemy, P., et al., "Compritol® 888 ATO: An Innovative Hot-Melt Coating Agent for Prolonged-Release Drug Formulations," *Europ. J. Pharmaceut. and Biopharmaceutics*, 47(1999)87-90.

Bhagwatwar, H., et al., "Preparation of Drug-Containing Wax Microspheres Using a Melt Dispersion Technique," *Pharmaceutical Research*, 6:7(1989)S-177, Abstract No. PD 1201.

Breitenbach, J., et al., "Solid Dispersions by an Integrated Melt Extrusion System," *Proceed. Int'l Symp. Control. Re. Bioact. Materials*, 25(1998)804-805.

Craig, D.Q.M., "The Physical Characterisation of Gelucire 50/13," *Bulletin Technique Gattefosse*, 89(1996)39-51.

DeMan, J.M., et al., "Thermal Analysis Microscopy for the Study of Phase Changes in Fats," *Food Microstructure*, 4(1985)233-239.

Eldem T., et al., "Polymorphic Behavior of Sprayed Lipid Micropellets and Its Evaluation by Differential Scanning Calorimetry and Scanning Electron Microscopy," *Pharmaceutical Research*, 8:2(1991)178-184.

Eldem, T., et al., "Optimization of Spray-Dried and -Congealed Lipid Micropellets and Characterization of Their Surface Morphology by Scanning Electron Microscopy," Pharmaceutical Research, 8:1(1991)47-54.

Emas, M., and H. Nyqvist, "Methods of Studying Aging and Stabilization of Spray-Congealed Solid Dispersions with Carnauba Wax. 1. Microcalorimetric Investigation," *Int'l J. Pharmaceutics*, 197(2000)117-127.

Faham, A., et al., "Hot-Melt Coating Technology. I. Influence of Compritol 888 Ato and Granule Size on Theophylline Release," *Drug Dev. Industrial Pharm.*, 26:2(2000)167-176.

Follonier, N., et al, "Hot-Melt Extruded Pellets for the Sustained Release of Highly Dosed Freely Soluble Drugs," *Proceed. Intern. Symp. Control. Release Bioactive Materials*, 18(1991)578-579.

Forster, A., et al., "Characterization of Glass Solutions of Poorly Water-Soluble Drugs Produced by Melt Extrusion with Hydrophilic Amorphous Polymers," *J. Pharmacy Pharmacology*, 53(2001)303-315.

Foulds, G., et al., "The Absence of an Effect of Food on the Bioavailability of Azithromycin Administered as Tablets, Sachet or Suspension," *J. Antimicrobial Chemotherapy*, 37:Suppl. C(1996)37-44.

Gattefosse, "Gelucire®—Pharmaceutical Excipients for Oral Semi-Solid Formulations," Technical Dossier, $2^{nd}$ edition, Gattefosse s.a., Cedex, France (1996).

Ghali, E.S., et al., "Thermal Treatment of Beads with Wax for Controlled Release," *Drug Development and Industrial Pharmacy*, 15:9(1989)1311-1328.

Hancock, B.C., and G. Zografi, "The Relationship Between the Glass Transition Temperature and the Water Content of Amorphous Pharmaceutical Solids," *Pharmaceutical Research*, 11:4(1994)471-477.

Joachim, J., et al., "Le Compritol, Etudes Galenique, Physique et Statstique," *APGI*, IV(1989)291-296.

Johnson, D.E., et al., "A New Method for Coating Glass Beads for Use in Gas Chromatography of Chloropromazine and Its Metabolites," Source unknown, and date unknown, (May be 1964-1965).

Jorgensen, K., et al., "Dissolution Stability of Multiparticulate Controlled Release Tablets," *Int'l J. Pharmaceutics*, 153(1997)1-11.

Meshall, M.M., et al., "Optimization of Theophylline Release from Tablets Containing Compritol," *S.T.P. Pharma Sciences*, 5:6(1995)429-434.

Perez, M. deLos A, et al., "Sustained Release Phenylpropanolamine Hydrochloride from Compritol ATO-888 Matrix," *Pharmaceutical Research*, 9:10(1992)S-162, Abstract No. PT6191.

Perez, M.A., et al., "Sustained Release Phenylpropanolamine Hydrochloride from ATO 888 Matrix," PRHSJ, 12:4(1993)263-267.

Perissutti, B., et al., "Solid Dispersions of Carbamazepine with Gelucire 44/14 and 50/13," *S.T.P. Pharma Sciences*, 10:6(2000)479-484.

Physician's Desk Reference, Information cited on ZITHROMAX® capsules (equivalent to 250 mg azithromycin), tablets (equivalent to 600 mg azithromycin), and oral suspension (equivalent to 1 g azithromycin).

Reilly, W.J. Jr., and J.B. Schwartz, "A Potential Controlled Release Wax Matrix Excipient," *Pharmaceutical Research*, 8:10(1991)98, supplement, Abstract No. PT6108.

Reis, R. and F. Moll, "Matrix Formation of Polyglycolic Acid Tablets by Annealing," *European J. Pharm. and Biopharm.*, 40:1(1994)14-18.

Rxlist.com, "Azithromycin," description of drug, categories, brand names, from internet website, Mar. 14, 2001.

San Vincente, A., et al., "Effect of Aging on the Release of Salbutamol Sulfate from Lipid Matrices," *Int'l J. Pharmaceutics*, 208(2000)13-21).

Schwartz, J.B., et al., "A Potential Controlled Release Wax Matrix Excipient for Tablets," *Pharmaceutical Research*, 9:10(1992)S-162, Abstract No. PT6189.

Schwartz, J.B., et al., Preliminary Evaluation of Controlled Release Agents for Tablets, *Pharmaceutical Research*, 9:10(1992)S-162, Abstract No. PT6190.

Sugao, H., et al, "Taste Masking of Bitter Drug Powder without Loss of Bioavailability by Heat Treatment of Wax-Coated Microparticles," *J. Pharmaceutical Sci.*, 87:1(1998)96-100.

Thomsen, L.J., et al., "Prolonged Release Matrix Pellets Prepared by Melt Pelletization. I. Process Variables," *Drug Development and Industrial Pharmacy*, 19:15(1993)187-1887.

Wang, A.E. and J.B. Schwartz, "Effect of Temperature on Drug Release from Wax Matrix Tablets After Thermal Treatment," *Pharmaceutical Research*, 11:10(1994)S-155, Abstract No. 6099.

Zhang, Y.-E., et al., Effect of Processing Methods and Heat Treatment on the Formation of Wax Matrix Tablets for Sustained Drug Release, *Pharm. Dev. Technol.*, 6:2(2001)131-144.

Arguendas, A., "Single Dose Therapy in Otitis Media, *Clinical Microbiology and Infection*," Abstract, S130, vol. 5, Supplemental 3, (1999).

Block, S., et al., "Single-Dose Azithromycin (30 mg/kg) in Acute Otitis Media," ICAAC, New Orleans, LA, Sep. 7-10, 2003, Abstract 174.

Curatolo, W., et al., "Site-Specific Absorption and Toleration of Azithromycin," Proceedings Intern. Symposium Rel. Bioact. Mater., 23, 1996.

Physicians Desk Reference, "*Appendix A Summary of Pediatric Suspension Commercial Products*," $55^{th}$ edition, Phase III Clinical Dosage Form Nomination, pp. 19 and 28 (2001).

Rodriguez et al., International Journal of Pharmaceutics, Jun. 1999, vol. 183, No. 2, pp. 133-143.

\* cited by examiner

MULTIPARTICULATE CRYSTALLINE DRUG COMPOSITIONS HAVING CONTROLLED RELEASE PROFILES

The present application claims the priority benefit of U.S. Provisional Application No. 60/527,329, filed on Dec. 4, 2003. The contents of the priority document are herein incorporated by reference.

BACKGROUND OF THE INVENTION

Multiparticulates are well known dosage forms that comprise a multiplicity of particles whose totality represents the intended therapeutically useful dose of a drug. When taken orally, multiparticulates generally disperse freely in the gastrointestinal (GI) tract, maximize absorption, and minimize side effects. See, for example, *Multiparticulate Oral Drug Delivery* (Marcel Dekker, 1994), and *Pharmaceutical Pelletization Technology* (Marcel Dekker, 1989).

A specific example is disclosed in Curatolo et al., U.S. Pat. No. 6,068,859, which discloses multiparticulates that provide controlled release of azithromycin.

Yet another example of a multiparticulate is disclosed in Burnside, U.S. 2001/0006650 A1, published Jul. 5, 2001, which discloses a solid solution beadlet. The beadlet comprises (i) a hydrophobic long chain fatty acid or ester component; (ii) a surfactant; and (iii) a therapeutic agent. The therapeutic agent such as a drug is described as being dissolved in the hydrophobic component to form a single phase solid solution.

Multiparticulates are often used to provide controlled-release of a drug. One problem when formulating a multiparticulate that controls the release of the drug is setting the release rate of the drug. The release rate of the drug depends on a variety of factors, including the carrier used to form the multiparticulate and the amount of drug in the multiparticulate. Often it is desired to provide a particular release rate. However, it may be difficult to achieve a particular release rate using a particular carrier composition.

Other formulation problems result from the melt-congeal process often used to form multiparticulates. The multiparticulates are preferably formed into round beads or spheres. However, some carriers, when melted and then solidified, do not form round beads. Instead, the carriers may solidify into rods, strings, or other non-spherical shapes, often referred to as "floss." The result is very irregularly shaped multiparticulates that are difficult to process into dosage forms.

It is also desired to maintain the chemical and physical stability of the drug in the multiparticulate. This is often best achieved by maintaining the crystallinity of the drug in the multiparticulate. Thus, it is desired to use carriers and processing conditions that avoid solubilization of the drug and so maintain the drug's crystallinity.

But the presence of substantial amounts of crystalline drug in the molten carrier during the melt-congeal process presents its own problem. The molten carrier containing the crystalline drug must be atomized to form multiparticulates. The presence of large amounts of crystalline drug in the molten mixture can lead to a high viscosity of the mixture, which in turn can make it difficult to process the molten mixture to form the multiparticulates.

Another constraint on the selection of carriers is that the drug may react with the materials used to form the multiparticulates. Since the melt-congeal process occurs at elevated temperatures, the materials should be inert at elevated temperatures as well. Thus, it is desired to use carriers that are relatively inert to reduce degradation of the drug or other excipients.

What is therefore desired is a multiparticulate composition which allows controlled release of the drug over a wide range of release rates, which allows the release rate to be set at a predetermined rate, which may be formed using a melt-congeal process, and which maintains the crystallinity of the drug during the melt-congeal process and in the resulting multiparticulate.

BRIEF SUMMARY OF THE INVENTION

In a first aspect of the invention, there is provided controlled release multiparticulates comprising crystalline drug, a glyceride having at least one alkylate substituent of at least 16 carbon atoms, and a poloxamer, wherein at least 70 wt % of the drug in the multiparticulate is crystalline.

In another aspect of the invention, there is provided a method for forming multiparticulates having the above-noted composition, comprising forming a molten mixture of the drug, the glyceride, and the poloxamer, forming droplets from the molten mixture and solidifying the droplets to form the multiparticulates.

In yet another alternative aspect of the invention, a method is provided for setting the release rate of a drug from a multiparticulate comprising forming a multiparticulate having the above-noted composition, but selecting a weight ratio of the poloxamer to the glyceride so as to achieve a desired release rate.

The multiparticulates of the present invention have several advantages over prior art multiparticulates. First, the particular glyceride/poloxamer mixture allows for extremely precise control of the release rate of the drug over a wide range of release rates. Small changes in the relative amounts of the glyceride and the poloxamer can result in large changes in the release rate of the drug. This allows the release rate of the drug from the multiparticulates to be customized to a given application by selecting the proper ratio of drug, glyceride and poloxamer. The glyceride/poloxamer mixture provides the further advantage of controllably releasing nearly all of the drug from the multiparticulate.

Another advantage of the multiparticulates of the invention is improved stability of the drug. The poloxamer component of the multiparticulate is very inert, thus minimizing degradation of the drug. In addition, drugs generally have a relatively low solubility in the glyceride/poloxamer mixture. Further, the glyceride/poloxamer mixture melts at a temperature that is relatively low compared with the melting point of most highly crystalline drugs. The glyceride/poloxamer mixture thus maintains the crystallinity of the drug during the melt-congeal process and in the resulting multiparticulate.

Yet another advantage of the present invention is that, in some embodiments, the glyceride/poloxamer mixture allows higher drug loading in the multiparticulate. By "drug loading" is meant the weight fraction of drug present in the multiparticulate. The combination of the glyceride and poloxamer provides a mixture which when molten has low viscosity and remains flowable even when it includes large weight fractions of crystalline drug.

The foregoing and other objectives, features, and advantages of the invention will be more readily understood upon consideration of the following detailed description of the invention.

DETAILED DESCRIPTION OF PREFERRED EMBODIMENTS

The multiparticulates comprise a crystalline drug, a glyceride having at least one alkylate substituent of at least 16 carbon atoms, and a poloxamer. At least 70 wt % of the drug in the multiparticulate is crystalline. Drugs suitable for use with the poloxamers and glycerides and methods for making the multiparticulates are detailed below.

The multiparticulates of the invention generally are of a mean diameter from about 40 to about 3,000 μm, with a preferred range of 50 to 1,000 μm, and most preferably from about 100 to 300 μm. While the multiparticulates can have any shape and texture, it is preferred that they be spherical, with a smooth surface texture. These physical characteristics of the multiparticulates improve their flow properties, permit them to be uniformly coated (if desired), and improve their "mouth feel" and ease of swallowing. As used herein, the term "about" means±10% of the value.

The multiparticulates of the present invention are particularly suitable for controlled release or delayed release or any combination of these two release profiles when introduced to a use environment. As used herein, a "use environment" can be either the in vivo environment of the GI tract, subdermal, intranasal, buccal, intrathecal, ocular, intraaural, subcutaneous spaces, vaginal tract, arterial and venous blood vessels, pulmonary tract or intramuscular tissue of an animal, such as a mammal and particularly a human, or the in vitro environment of a test solution. Exemplary test solutions include aqueous solutions at 37° C. comprising (1) 0.1 N HCl, simulating gastric fluid without enzymes; (2) 0.01 N HCl, simulating gastric fluid that avoids excessive acid degradation of azithromycin, and (3) 50 mM $KH_2PO_4$, adjusted to pH 6.8 using KOH or 50 mM $Na_3PO_4$, adjusted to pH 6.8 using NaOH, both of which simulate intestinal fluid without enzymes. The inventors have also found that for some formulations, an in vitro test solution comprising 100 mM $Na_2HPO_4$, adjusted to pH 6.0 using NaOH provides a discriminating means to differentiate among different formulations on the basis of dissolution profile. It has been determined that in vitro dissolution tests in such solutions provide a good indicator of in vivo performance and bioavailability. Further details of in vitro tests and test solutions are described herein.

Drugs

The drug may be any drug that may be administered in a crystalline form in a multiparticulate. The term "drug" as used in this specification and the accompanying claims includes, by way of example and not of limitation, any physiologically or pharmacologically active substance that produces a localized or systemic effect in animals. The term "animals" is meant to include mammals, including human beings.

Examples of crystalline drugs employed in the devices of this invention include, without limitation, inorganic and organic compounds that act on the peripheral nerves, adrenergic receptors, cholinergic receptors, nervous system, skeletal muscles, cardiovascular smooth muscles, blood circulatory system, synaptic sites, neuroeffector junctional sites, endocrine and hormone systems, immunological system, reproductive system, autocoid systems, alimentary and excretary systems, inhibitors of autocoids and histamine systems. Preferred classes of drugs include, but are not limited to, antihypertensives, antianxiety agents, anticlotting agents, anticonvulsants, blood glucose-lowering agents, decongestants, antihistamines, antitussives, antineoplastics, beta blockers, anti-inflammatories, antipsychotic agents, cognitive enhancers, anti-atherosclerotic agents, cholesterol-reducing agents, antiobesity agents, autoimmune disorder agents, anti-impotence agents, antibacterial and antifungal agents, hypnotic agents, anti-Parkinsonism agents, anti-Alzheimer's disease agents, antibiotics, anti-depressants, and antiviral agents, glycogen phosphorylase inhibitors, and cholesterol ester transfer protein inhibitors.

Each named drug should be understood to include the neutral form of the drug and pharmaceutically acceptable forms thereof. By "pharmaceutically acceptable forms" thereof is meant any pharmaceutically acceptable derivative or variation, including stereoisomers, stereoisomer mixtures, enantiomers, solvates, hydrates, isomorphs, polymorphs, salt forms and prodrugs. Specific examples of antihypertensives include prazosin, nifedipine, amlodipine besylate, trimazosin and doxazosin; specific examples of a blood glucose-lowering agent are glipizide and chlorpropamide; a specific example of an anti-impotence agent is sildenafil and sildenafil citrate; specific examples of antineoplastics include chlorambucil, lomustine and echinomycin; a specific example of an imidazole-type antineoplastic is tubulazole; a specific example of an anti-hypercholesterolemic is atorvastatin and atorvastatin calcium; specific examples of anxiolytics include hydroxyzine hydrochloride and doxepin hydrochloride; specific examples of anti-inflammatory agents include betamethasone, prednisolone, aspirin, piroxicam, valdecoxib, carprofen, celecoxib, flurbiprofen and (+)-N-{4-[3-(4-fluorophenoxy)phenoxy]-2-cyclopenten-1-yl}-N-hyroxyurea; a specific example of a barbiturate is phenobarbital; specific examples of antivirals include acyclovir, nelfinavir, and virazole; specific examples of vitamins/nutritional agents include retinol and vitamin E; specific examples of beta blockers include timolol and nadolol; a specific example of an emetic is apomorphine; specific examples of a diuretic include chlorthalidone and spironolactone; a specific example of an anticoagulant is dicumarol; specific examples of cardiotonics include digoxin and digitoxin; specific examples of androgens include 17-methyltestosterone and testosterone; a specific example of a mineral corticoid is desoxycorticosterone; a specific example of a steroidal hypnotic/anesthetic is alfaxalone; specific examples of anabolic agents include fluoxymesterone and methanstenolone; specific examples of antidepression agents include sulpiride, [3,6-dimethyl-2-(2,4,6-trimethyl-phenoxy)-pyridin-4-yl]-(1-ethylpropyl)-amine, 3,5-dimethyl-4-(3'-pentoxy)-2-(2',4', 6'-trimethylphenoxy)pyridine, pyroxidine, fluoxetine, paroxetine, venlafaxine and sertraline; specific examples of antibiotics include carbenicillin indanylsodium, bacampicillin hydrochloride, troleandomycin, doxycyline hyclate, ampicillin, amoxicillin and penicillin G; specific examples of anti-infectives include benzalkonium chloride and chlorhexidine; specific examples of coronary vasodilators include nitroglycerin and mioflazine; a specific example of a hypnotic is etomidate; specific examples of carbonic anhydrase inhibitors include acetazolamide and chlorzolamide; specific examples of antifungals include econazole, terconazole, fluconazole, voriconazole, and griseofulvin; a specific example of an antiprotozoal is metronidazole; specific examples of anthelmintic agents include thiabendazole and oxfendazole and morantel; specific examples of antihistamines include astemizole, levocabastine, cetirizine, decarboethoxylorata-dine and cinnarizine; specific examples of antipsychotics include ziprasidone, olanzepine, thiothixene hydrochloride, fluspirilene, risperidone and penfluridole; specific examples of gastrointestinal agents include loperamide and cisapride; specific examples of serotonin antagonists include ketanserin and mianserin; a specific example of an anesthetic is lidocaine; a specific example of a hypoglycemic agent is acetohexamide; a specific example of an anti-emetic is dimenhydrinate; a specific example of an antibacterial is cotrimoxazole; a specific example of a dopaminergic agent is L-DOPA; specific examples of anti-Alzheimer's Disease agents are THA and donepezil; a specific example of an anti-ulcer agent/H2 antagonist is famotidine; specific examples of sedative/hypnotic agents include chlordiazepoxide and triazolam; a specific example of a vasodilator is alprostadil; a specific example of a platelet inhibitor is prostacyclin; specific examples of ACE inhibitor/antihypertensive agents include enalaprilic acid, quinapril, and lisinopril; specific examples of tetracycline antibiotics include oxytetracycline and minocycline; specific examples of macrolide antibiotics include erythromycin, clarithromycin, and spiramycin; a specific example of an azalide antibiotic is azithromycin; specific examples of glycogen phosphorylase inhibitors include [R—(R'S')]-5-chloro-N-[2-hydroxy-3-{methoxymethylamino}3-oxo-1-(phenylmethyl)propyl-1H-indole-2-carboxamide and 5-chloro-1H-indole-2-carboxylic acid [(1S)-benzyl-(2R)-hydroxy-3-((3R,4S)-dihydroxy-pyrrolidin-1-yl-)-3-oxypropyl]amide; and specific examples of cholesterol ester transfer protein inhibitors include [2R,4S]-4-[acetyl-(3,5-bis-trifluoromethyl-benzyl)-amino]-2-ethyl-6-trifluoromethyl-3,4-dihydro-2H-quinoline-1-carboxylic acid isopropyl ester, [2R,4S]-4-[3,5-bis-trifluoromethyl-benzyl)-methoxycarbonyl-amino]-2-ethyl-6-trifluoromethyl-3,4-dihydro-2H-quinoline-1-carboxylic acid ethyl ester, and [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid isopropyl ester.

Glycerides

A principal component of the multiparticulate is a glyceride having at least one alkylate substituent of at least 16 carbon atoms. Exemplary glycerides include mono-, di- and trialkyl glycerides of palmitate, stearate, oleate, linoleate, arachidate, behenate, lignocerate, ricinoleate, and mixtures thereof. Exemplary commercial grades of glycerides include: COMPRITOL 888 ATO, available from Gattefossé Corporation of Paramus, N.J., which is a mixture of 13 to 21 wt % glyceryl monobehenate, 40 to 60 wt % glyceryl dibehenate, and about 35 wt % glyceryl tribehenate; DYNASAN 118, available from Hüls America, Inc. of Piscataway, N.J., which is a glyceryl tristearate; STEROTEX NF, available from Karishamns USA Inc. of Columbus, Ohio, which is an hydrogenated cotton seed oil made up of about 22 wt % glyceryl tripalmitate and less than 76 wt % glyceryl tristearate; LUBRITAB®, available from Edward Mendell Co. of Patterson, N.Y., is a hydrogenated refined cottonseed oil made up of about 28-32 wt % glyceryl tripalmitate and 58-62 wt % glyceryl tristearate; HYDROKOTE, available from Karishamns USA, which is a partially hydrogenated soybean oil made up of about 26 wt % oleate, 49 wt % linoleate, 11 wt % linolenate before hydrogenation; CASTOR WAX, available from NL Industries, Inc., which is hydrogenated castor oil consisting mainly of the trialkyl glyceride of hydroxystearic acid before hydrogenation; SYNCROWAX HR-C, available from Croda, Inc. of New York, N.Y., which is a glyceryl tribehenate; and SYNCROWAX HGL-C also available from Croda, which is a mixture of $C_{18}$ to $C_{36}$ trialkyl glycerides.

Preferred glycerides include (1) mixtures of glyceryl mono-, di-, and tribehenate; (2) mixtures of glyceryl tripalmitate and glyceryl tristearate; (3) glyceryl tribehenate; and mixtures of the three.

Preferably, the glyceride has a melting point of at least about 50° C., and more preferably at least about 60° C. The melting point should be less than about 150° C. to avoid drug degradation at high processing temperatures.

Poloxamers

Another key component of the multiparticulate is a particular class of solid polyoxyethylene-polyoxypropylene block copolymers, also known in the pharmaceutical arts as "poloxamers." Poloxamers are selected so as to avoid solubilization of the crystalline drug in the multiparticulate. Such poloxamers generally have a molecular weight ranging from about 2000 to about 15,000 daltons and have the general formula:

wherein a is about 10 to about 150, representing blocks of repeat units of polyoxyethylene, and b is about 20 to about 60, representing blocks of repeat units of polyoxypropylene, depending on the particular grade. Suitable poloxamers are sold under the trade names PLURONIC and LUTROL available from BASF Corporation of Mt. Olive, N.J. Preferred poloxamers have a molecular weight of at least about 4,700 daltons and a melting point of at least about 45° C. and so are solid at ambient temperatures. Being solid at ambient temperatures has several advantages. First, the crystalline drug has a lower solubility in solid poloxamers relative to liquid poloxamers, and thus the drug is more likely to remain in its crystalline form and not dissolve in the carrier. Second, the use of a solid poloxamer provides improved physical stability of the multiparticulate relative to the use of a liquid poloxamer primarily because the mobility of the solid poloxamer is lower than that of a liquid poloxamer, resulting in a reduced rate of change in the morphology of the multiparticulate.

Preferred grades of poloxamers include poloxamer 188 (PLURONIC F68), poloxamer 237 (PLURONIC F87), poloxamer 338 (PLURONIC F108), poloxamer 407 (PLURONIC F127), the specifications of which are given in Table A, and mixtures of those poloxamers.

TABLE A

| Poloxamer | Physical Form at 25° C. | a | B | Average Molecular Weight (daltons) |
|---|---|---|---|---|
| 188 | Solid | 80 | 27 | 7,680-9,510 |
| 237 | Solid | 64 | 37 | 6,840-8,830 |

TABLE A-continued

| Poloxamer | Physical Form at 25° C. | a | B | Average Molecular Weight (daltons) |
|---|---|---|---|---|
| 338 | Solid | 141 | 44 | 12,700-17,400 |
| 407 | Solid | 101 | 56 | 9,840-14,600 |

Beyond their desirability from the standpoint of not solubilizing crystalline drug, such poloxamers have several other advantages for use in a multiparticulate. They are very inert and so their use reduces the risk of degradation of the drug or other excipients, even at the elevated temperatures used to form the multiparticulates. Such poloxamers also solidify quickly and tend not to form floss when used with the glyceride component of the multiparticulates, thereby providing smoother, more rounded beads, which are easier to process.

Controlled Release

The combination of the glyceride and the poloxamer in the multiparticulate allows for the precise control of the release rate of the drug from the multiparticulate to a use environment. The glyceride is a hydrophobic material that, by itself, dissolves, disperses, or erodes slowly in a use environment such as the GI tract. The poloxamer is a hydrophilic material that acts as a dissolution enhancer in the multiparticulate to speed the release of the drug, yet not permit its immediate release. The addition of a small amount of poloxamer to the glyceride can result in large changes in the release rate of the drug.

The drug release from a multiparticulate may be modeled as a first order process in which the dissolution rate constant, k, may be determined by equation I:

$$A_t = A_\infty \cdot [1 - e^{-kt}] \quad (I)$$

where $A_t$ is the percentage of drug released from the multiparticulates at time t, $A_\infty$ is the percentage of drug released from the multiparticulates over a long period of time (such as the amount released at 180 minutes plus the amount remaining in the multiparticulates), t is the time in minutes, and k is the dissolution rate constant in $min^{-1}$. The present invention has the advantage that small changes in the amount of the poloxamer present in the glyceride lead to relatively large changes in the rate constant k. For example, for a composition comprising 50 wt % azithromycin dihydrate and 50 wt % of a mixture of COMPRITOL 888 ATO and LUTROL F127, changing the poloxamer to glyceride ratio 2.1-fold (from 0.042 to 0.087 w/w) leads to a change in the dissolution rate constant of 1.9-fold (from 0.009 $min^{-1}$ to 0.017 $min^{-1}$). Similar control over the release rates can be obtained for other drugs, with the magnitude of the control being dependent on several factors including (1) the nature of the drug, (2) the drug loading in the multiparticulate, and (3) the poloxamer to glyceride ratio.

Other equations known in the art can also be used to describe the rate of release of drugs from multiparticulates. Such equations often require the fitting of the data so that one or more constants that describe the drug release rate can be determined.

The dissolution rate of drug from a multiparticulate may also be characterized by the amount released at a specified time following introduction of the multiparticulate to a use environment. The specified time may be selected as convenient for determining the release rate of drug from the multiparticulate. Typically, times such as 30 minutes or 60 minutes are selected for determining the amount released from the multiparticulate. To determine the amount released, the multiparticulates are introduced to an aqueous environment of use and the use environment is sampled at the selected time and analyzed for the amount of drug released by analytical methods known in the art, such as high-performance liquid chromatograph (HPLC) analysis. The amount released may be reported as the mass of drug released, as the fraction or percentage of drug initially present in the multiparticulate released, or by some other convenient measure.

The dissolution rate of drug from a multiparticulate may also be characterized by the time required for half of the drug to be released from the multiparticulate following introduction to a use environment. This value, $t_{1/2}$, may be determined by measuring the amount of drug released versus time following introduction to an aqueous environment of use using methods known in the art.

The particular combination of glyceride and poloxamer also results in a multiparticulate that yields substantially complete release of the drug. Drug that remains with the multiparticulate and not released to the use environment is termed "residual drug." The amount of residual drug present after 30 hours in a use environment, such as in the GI tract or in an IB solution, is often less than 10 wt %, may be less than 5 wt %, and may even be as little as less than 1 wt %. That is, the multiparticulate releases at least 90 wt % of the drug, at least 95 wt % of the drug, or even at least 99 wt % of the drug within about 30 hours after administration to the use environment.

The amount of drug released may be determined either by in vivo tests or by suitable in vitro tests, such as a dissolution test in the in vitro test solutions previously described.

The combination of the glyceride and the poloxamer also provides a mixture that has several excellent properties for forming multiparticulates when using a melt-congeal process. The glyceride/poloxamer mixture works well with a wide range of drugs. The mixture is solid at ambient conditions but has a low melting point. The melting point of a mixture of the glyceride and poloxamer is preferably greater than about 40° C., more preferably greater than about 50° C., and most preferably greater than about 60° C. Typically, the glyceride/poloxamer mixture will have a melting point ranging from about 70° C. to 90° C. This relatively low melt temperature reduces the risk of degradation of the drug: In addition, the melt temperature is well below the melting point of most crystalline drugs.

The combination of the glyceride and the poloxamer has a further advantage in that the molten mixture has a relatively low viscosity, even at high drug loading. It is preferred that the viscosity of the molten feed be at least about 1 cp and less than about 10,000 cp, more preferably at least 50 cp and less than about 1000 cp. As discussed above, one problem when forming multiparticulates using the melt congeal method is that the molten mixture must be flowable so as to be transported to an atomizer and atomized to form beads. The crystalline drug suspended in the molten mixture reduces the flowability of the molten mixture, particularly as the amount of drug in the molten mixture increases. The combination of the glyceride and poloxamer results in a molten mixture that has low viscosity and good flowing characteristics, even at drug loadings as high as 70 wt %.

The glyceride/poloxamer mixture can exist as separate regions or phases of poloxamer and glyceride, as a solid solution, that is, a single phase in which the poloxamer is homogeneously distributed throughout the glyceride, or any combination of these states or states that are intermediate them. In one embodiment, the poloxamer is present in separate regions or phases that are dispersed substantially homogeneously throughout the carrier, as shown for example, schematically in FIG. 1. Such glyceride/poloxamer mixtures generally have improved dissolution properties in terms of variation in the release rate and minimization of residual drug.

In one embodiment, the multiparticulates comprise substantially crystalline drug particles substantially embedded in a glyceride/poloxamer mixture, meaning that at least about 90 wt % of the drug particles in the multiparticulate are entirely surrounded by the glyceride/poloxamer mixture and are not exposed to the outside surface of the multiparticulate. Preferably at least about 95 wt %, and more preferably at least about 98 wt %, and most preferably about 100 wt % of the drug particles are entirely surrounded or encapsulated by the glyceride/poloxamer mixture. The crystalline drug particles are distributed throughout the glyceride/poloxamer mixture. The poloxamer is uniformly distributed throughout the glyceride and is present in substantially separate regions (that is, as a substantially separate phase). The multiparticulates therefore comprise at least three separate and distinct phases: (1) crystalline drug, (2) the water-insoluble glyceride, and (3) the poloxamer, which acts as a water-soluble or dispersible dissolution enhancer. In this embodiment, the poloxamer is in the form of narrow channels or fibers within the multiparticulate. These channels or fibers have a mean diameter ranging from about 0.1 to about 30 μm. The narrow channels or fibers interconnect the drug crystals present in the multiparticulate.

Figure 1:
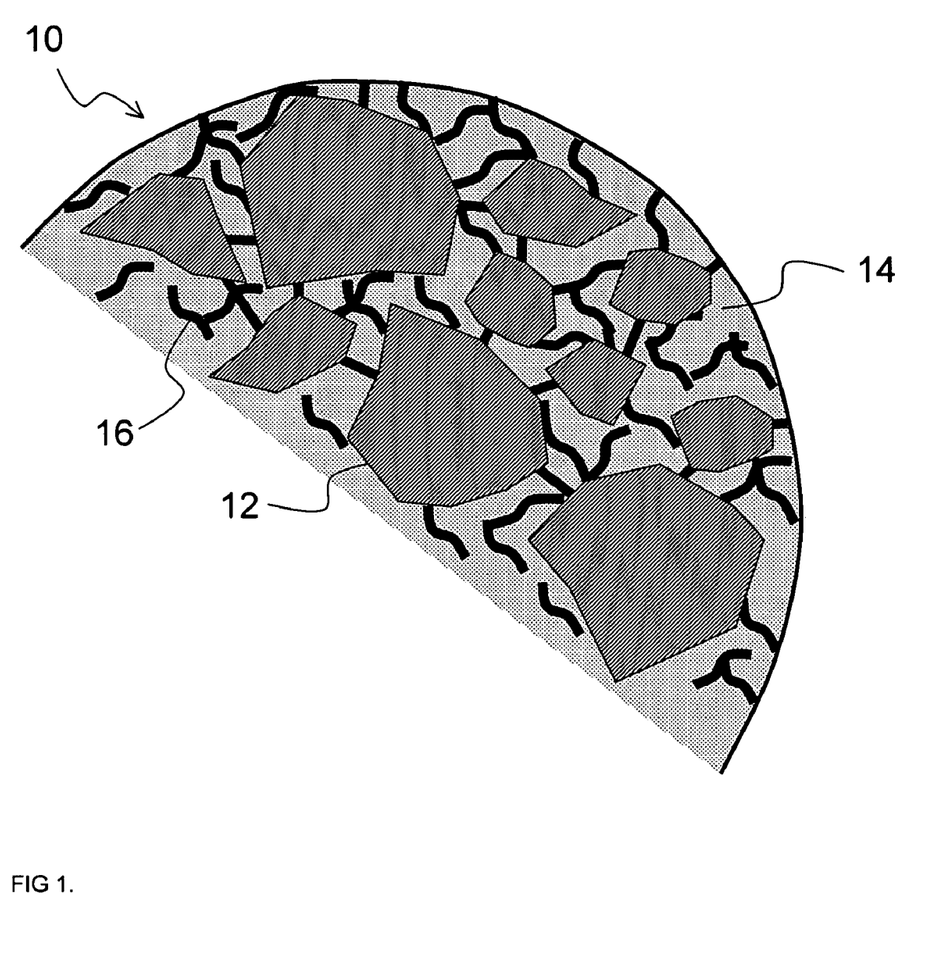
FIG. 1 shows a cross-sectional schematic of a multiparticulate prior to exposure to a use environment.

FIG. 1 shows a cross-sectional schematic of a multiparticulate 10 prior to exposure to a use environment. The multiparticulate comprises crystalline drug particles 12 embedded in the glyceride/poloxamer mixture. The poloxamer 16 is substantially homogeneously distributed throughout the glyceride 14. The poloxamer 16 is present as a separate phase from the glyceride 14.

Figure 2:
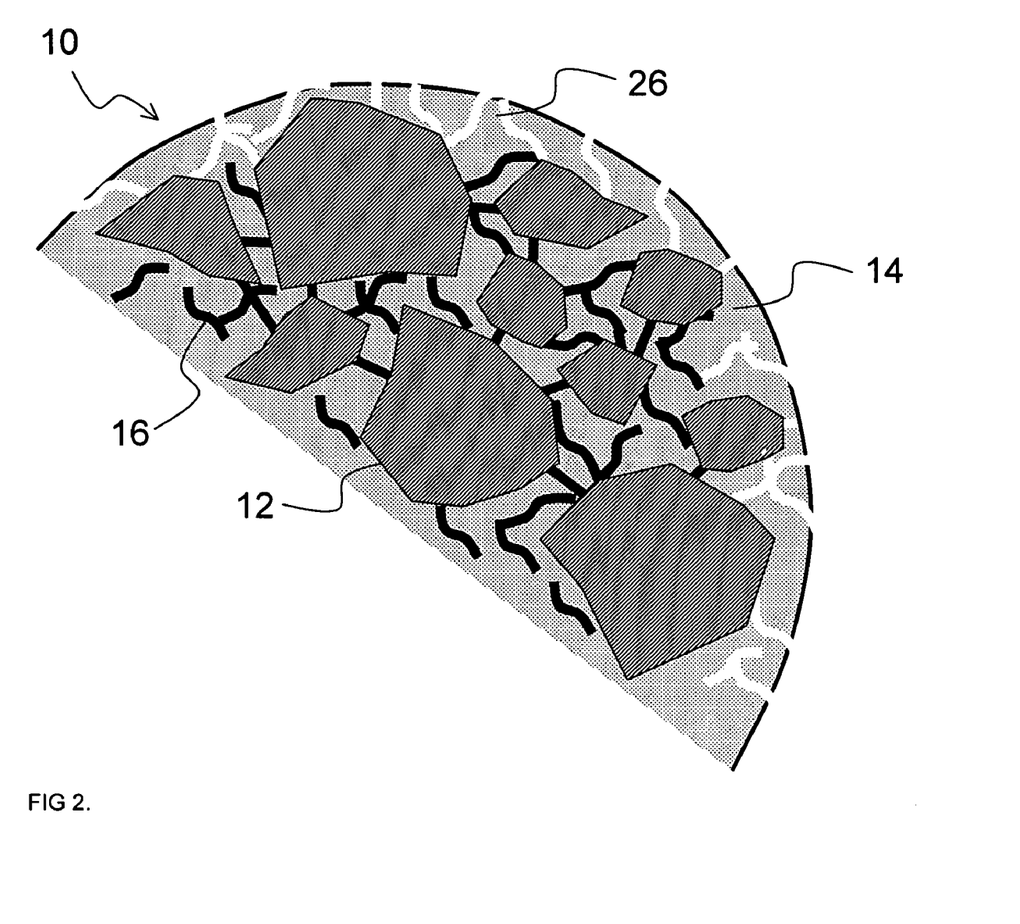
FIG. 2 shows a cross-sectional schematic of the multiparticulate of FIG. 1 after initial exposure to an aqueous environment of use.

When such a multiparticulate is placed into an aqueous environment of use, water dissolves or disperses the poloxamer 16, resulting in the formation of pores or channels 26. See FIGS. 2-3, which are schematics of the multiparticulate of FIG. 1 after initial and prolonged exposure to an aqueous environment of use, respectively. These pores or channels provide access of the water in the aqueous environment of use to the embedded drug crystals, resulting in dissolution of drug from the multiparticulate through these pores or channels 26. As drug crystals 12 dissolve, they provide larger cavities that provide water from the use environment access to additional poloxamer 16, forming more pores or channels 26 and, in turn, access to more drug crystals 12 embedded in the multiparticulate.

Figure 3:
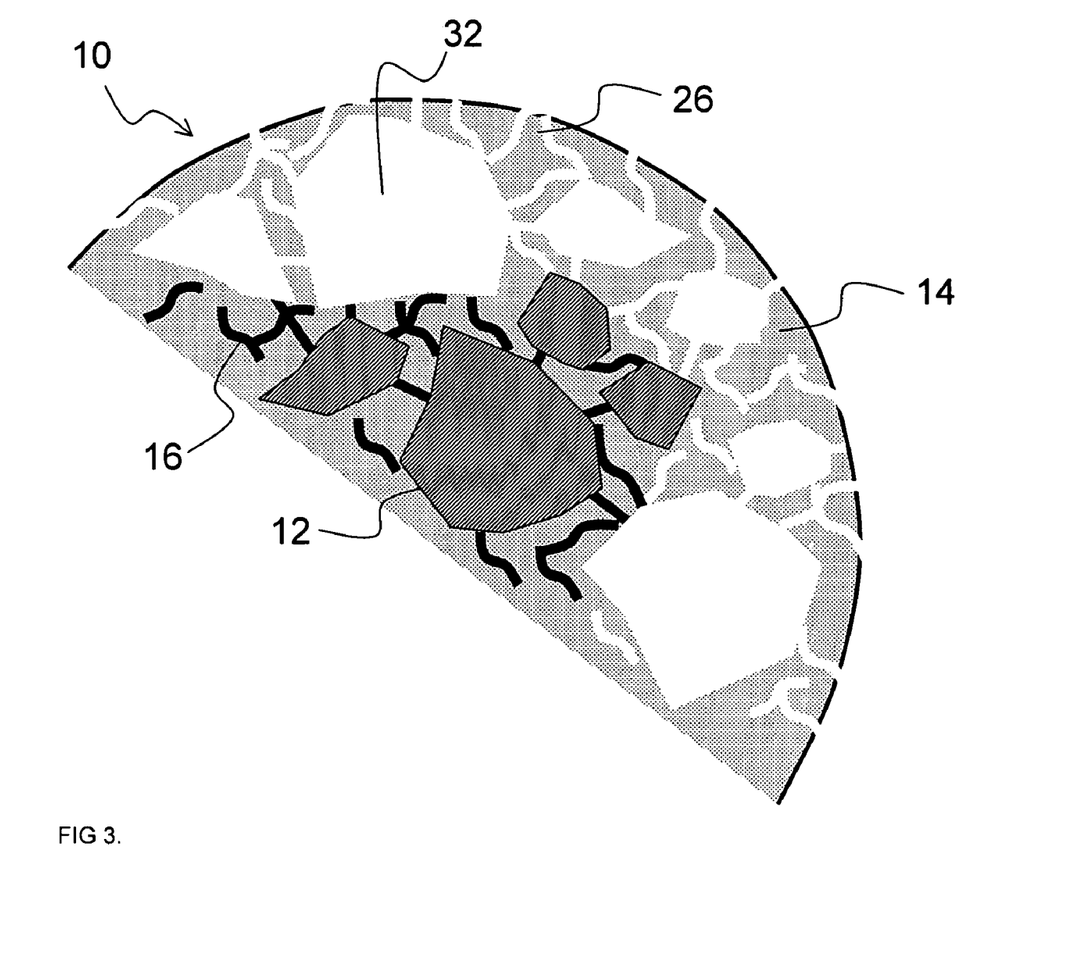
FIG. 3 shows a cross-sectional schematic of the multiparticulate of FIG. 1 after prolonged exposure to an aqueous environment of use.

As shown in FIG. 3, after prolonged exposure to an aqueous environment of use, some of the crystalline drug particles 12 have completely dissolved, leaving behind cavities 32. The cavities 32 expose additional amounts of the poloxamer 16 and crystalline drug particles 12 located inside the multiparticulate to the use environment. Over time, substantially all of the crystalline drug particles dissolve and are released to the aqueous environment of use. By controlling the relative amount of poloxamer to glyceride, the number of channels or pores 26 may be controlled, thus directly affecting the release of dissolved drug from the multiparticulate.

The relative amounts of drug, glyceride and poloxamer may be varied to achieve the desired dose of drug and release rate. In general, the drug may range from about 5 to about 90 wt % of the multiparticulate, preferably about 10 to 80 wt %, more preferably about 30 to 60 wt % of the multiparticulate. In one embodiment, the multiparticulate has a high drug loading in which the drug is at least 40 wt % of the multiparticulate. The amount of glyceride may range from about 10 to about 95 wt % of the multiparticulate, preferably about 20 to about 90 wt %, more preferably about 40 to about 60 wt % of the multiparticulate. The amount of poloxamer may range from about 0.1 to about 30 wt % of the multiparticulate. The weight ratio of poloxamer to glyceride typically ranges from about 0.01 to about 0.50, depending on the desired release rate. Generally, the higher the ratio of poloxamer to glyceride, the faster the rate of release of drug from the multiparticulate. For example, to obtain a $t_{1/2}$ of about 30 minutes with a multiparticulate comprising about 50 wt % drug, the poloxamer to glyceride ratio should be about 0.1. To obtain a $t_{1/2}$ of about 10 minutes with a multiparticulate comprising about 50 wt % drug, the poloxamer to glyceride ratio should be about 0.25. Where the poloxamer has a low melting point, the relative amounts of drug, glyceride, poloxamer and other excipients are chosen so that the resulting multiparticulate is solid under ambient conditions.

The multiparticulates comprise (1) crystalline drug suspended in (2) the glyceride/poloxamer mixture. The amount of drug that is crystalline should be at least 70 wt % of the total amount of drug present in the multiparticulate. Since physical and chemical stability of the drug tends to improve with increasing amounts of crystalline drug, in some embodiments it is preferred that the amount of drug that is crystalline is at least 80 wt %, and more preferably at least 90 wt %. The amount of drug that is crystalline in the multiparticulate may be determined by any conventional technique, such as by Powder X-Ray Diffraction (PXRD).

To maintain a high degree of drug crystallinity, the drug preferably has a low solubility in the molten glyceride/poloxamer mixture. This low solubility will minimize the formation of amorphous drug during the multiparticulate formation process. Preferably, the solubility of drug in the glyceride/poloxamer mixture at the processing conditions is less than about 20 wt %, more preferably less than about 10 wt %, even more preferably less than about 5 wt %. By "solubility of drug in the glyceride/poloxamer mixture" is meant the mass of drug dissolved in the glyceride/poloxamer mixture divided by the total mass of glyceride, poloxamer, and dissolved drug. The solubility of drug in the glyceride/poloxamer mixture may be measured by slowly adding crystalline drug to a molten sample of the glyceride/poloxamer mixture and determining the point at which drug will no longer dissolve in the molten sample, either visually or through quantitative analytical techniques, such as light scattering. Alternatively, an excess of crystalline drug may be added to a sample of the molten glyceride/poloxamer mixture to form a suspension. This suspension may then be filtered or centrifuged to remove any undissolved crystalline drug and the amount of drug dissolved in the liquid phase can be measured using standard quantitative techniques, such as by HPLC. When performing such tests, care should be taken to ensure the form of the drug remains the same throughout the duration of the test. For example, if the drug is present as a crystalline hydrate, the molten glyceride/poloxamer mixture should contain a sufficient amount of water such that the crystalline drug does not dehydrate while measuring the solubility of the drug in the glyceride/poloxamer mixture. This can be accomplished, for example, by adding water to the molten carrier, by maintaining a high concentration of water vapor in the atmosphere above the melt, or both. Processes to maintain the desired crystalline form of the drug while forming multiparticulates are disclosed more fully in commonly assigned U.S. patent application Ser. No. 11/003,659 ("Method for Making Pharmaceutical Multiparticulates," filed concurrently herewith.

In addition to the glyceride and poloxamer the multiparticulates may include other excipients known in the art. One useful class of excipients includes those capable of modifying the viscosity of the molten mixture used to form the multiparticulates. Such viscosity-adjusting excipients may make up from 0 to about 25 wt % of the multiparticulate, based on the total mass of the multiparticulate. As described above, the viscosity of the molten mixture is a key variable in obtaining multiparticulates with a narrow particle size distribution. If the viscosity of the molten mixture is outside of the preferred viscosity ranges given above, a viscosity-adjusting excipient can be added to obtain a molten mixture within the preferred viscosity range. Examples of viscosity-reducing excipients include stearyl alcohol, cetyl alcohol, low molecular weight polyethylene glycol (i.e., less than about 1000 daltons), isopropyl alcohol, and water. Examples of viscosity-increasing excipients include microcrystalline wax, paraffin wax, synthetic wax, high molecular weight polyethylene glycols (i.e., greater than about 20,000 daltons), ethyl cellulose, hydroxypropyl cellulose, hydroxypropyl methyl cellulose, methyl cellulose, silicon dioxide, microcrystalline cellulose, magnesium silicate, sugars, and salts.

Other excipients may be added to adjust the release characteristics of the multiparticulates or to improve processing and typically make up from 0 to about 50 wt % of the multiparticulate, based on its total mass. For example, since the solubility of some drugs in aqueous solution decreases with increasing pH, a base may be included in the composition to decrease the rate at which such drugs are released in an aqueous use environment. Examples of bases that can be included in the composition include di- and tribasic sodium phosphate, di- and tribasic calcium phosphate, mono-, di-, and triethanolamine, sodium bicarbonate, sodium citrate dihydrate, and amine-functionalized methacrylate polymers and copolymers, such as EUDRAGIT E100 from Röhm Pharma of Darmstadt, Germany as well as other oxide, hydroxide, phosphate, carbonate, bicarbonate and citrate salts, including various hydrated or anhydrous forms known in the art. Still other excipients may be added to reduce the static charge on the multiparticulates; examples of such antistatic agents include talc and silicon dioxide. Flavorants, colorants, and other excipients may also be added in their usual amounts for their usual purposes.

Preparation of Multiparticulates

The multiparticulates are made via a melt-congeal process comprising the steps: (a) forming a molten mixture comprising the drug, the glyceride and the poloxamer; (b) delivering the molten mixture of step (a) to an atomizing means to form droplets from the molten mixture; and (c) congealing the droplets from step (b) to form multiparticulates.

The processing conditions are chosen to maintain the crystallinity of the drug. The temperature of the molten mixture is kept below the melting point of the drug. Preferably, at least 70 wt % of the drug remains crystalline within the molten feed, more preferably, at least 80 wt % and most preferably at least 90 wt %.

The term "molten mixture" as used herein refers to a mixture of drug, glyceride, and poloxamer heated sufficiently that the mixture becomes sufficiently fluid that the mixture may be formed into droplets or atomized. Atomization of the molten mixture may be carried out using any of the atomization methods described below. Generally, the mixture is molten in the sense that it will flow when subjected to one or more forces such as pressure, shear, and centrifugal force, such as that exerted by a centrifugal or spinning-disk atomizer. Thus, the drug/glyceride/poloxamer mixture may be considered "molten" when any portion of the drug/glyceride/poloxamer mixture becomes sufficiently fluid that the mixture, as a whole, may be atomized. Generally, a mixture is sufficiently fluid for atomization when the viscosity of the molten mixture is less than about 20,000 cp, preferably less than about 15,000 cp, and most preferably less than about 10,000 cp. Often, the mixture becomes molten when the mixture is heated above the melting point of the glyceride/poloxamer mixture, in cases where the glyceride/poloxamer mixture is sufficiently crystalline to have a relatively sharp melting point; or, when the glyceride/poloxamer mixture is amorphous, above the softening point of the glyceride/poloxamer mixture. The molten mixture is therefore often a suspension of solid particles in a fluid matrix. In one preferred embodiment, the molten mixture comprises a mixture of substantially crystalline drug particles suspended in a glyceride/poloxamer mixture that is substantially fluid. In such cases, a portion of the drug may be dissolved in the glyceride/poloxamer mixture and a portion of the glyceride/poloxamer mixture may remain solid.

Virtually any process may be used to form the molten mixture. One method involves heating the glyceride/poloxamer mixture in a tank until it is fluid and then adding the drug to the molten glyceride/poloxamer mixture. Generally, the glyceride/poloxamer mixture is heated to a temperature of about 10° C. or more above the temperature at which it becomes fluid. When one or more of the glyceride/poloxamer components is crystalline, this is generally about 10° C. or more above the melting point of the lowest melting point material of the mixture. The process is carried out so that at least a portion of the feed remains fluid until atomized. Once the glyceride/poloxamer mixture has become fluid, the drug may be added to the fluid carrier or "melt." Although the term "melt" generally refers specifically to the transition of a crystalline material from its crystalline to its liquid state, which occurs at its melting point, and the term "molten" generally refers to such a crystalline material in its fluid state, as used herein, the terms are used more broadly, referring in the case of "melt" to the heating of any material or mixture of materials sufficiently that it becomes fluid in the sense that it may be pumped or atomized in a manner similar to a crystalline material in the fluid state. Likewise "molten" refers to any material or mixture of materials that is in such a fluid state. Alternatively, the drug, the glyceride, and the poloxamer may be added to the tank and the mixture heated until the mixture has become fluid.

Once the glyceride/poloxamer mixture has become fluid and the drug has been added, the molten mixture is mixed to ensure the drug is uniformly distributed therein. Mixing is generally done using mechanical means, such as overhead mixers, magnetically driven mixers and stir bars, planetary mixers, and homogenizers. Optionally, the contents of the tank can be pumped out of the tank and through an in-line, static mixer or extruder and then returned to the tank. The amount of shear used to mix the molten feed should be sufficiently high to ensure uniform distribution of the drug in the molten carrier. The amount of shear is kept low enough so the form of the drug does not change, i.e., so as to cause an increase in the amount of amorphous drug or a change in the crystalline form of the drug. It is also preferred that the shear not be so high as to reduce the particle size of the drug crystals. The molten mixture can be mixed from a few minutes to several hours, the mixing time being dependent on the viscosity of the feed and the solubility of drug and any optional excipients in the carrier.

An alternative method of preparing the molten mixture is to use two tanks, melting either the glyceride or the poloxamer in one tank and the other component in another tank. The drug is added to one of these tanks and mixed as described above. The two melts are then pumped through an in-line static mixer or extruder to produce a single molten mixture that is directed to the atomization process described below.

Another method that can be used to prepare the molten mixture is to use a continuously stirred tank system. In this system, the drug, glyceride, and poloxamer are continuously added to a heated tank equipped with means for continuous stirring, while the molten feed is continuously removed from the tank. The contents of the tank are heated such that the temperature of the contents is about 10° C. or more above the melting point of the carrier. The drug, glyceride, and poloxamer are added in such proportions that the molten mixture removed from the tank has the desired composition. The drug is typically added in solid form and may be pre-heated prior to addition to the tank. The glyceride and poloxamer may also be preheated or even pre-melted prior to addition to the continuously stirred tank system.

An especially preferred method of forming the molten mixture is by an extruder. By "extruder" is meant a device or collection of devices that creates a molten extrudate by heat and/or shear forces and/or produces a uniformly mixed extrudate from a solid and/or liquid (e.g., molten) feed. Such devices include, but are not limited to single-screw extruders; twin-screw extruders, including co-rotating, counter-rotating, intermeshing, and non-intermeshing extruders; multiple screw extruders; ram extruders, consisting of a heated cylinder and a piston for extruding the molten feed; gear-pump extruders, consisting of a heated gear pump, generally counter-rotating, that simultaneously heats and pumps the molten feed; and conveyer extruders. Conveyer extruders comprise a conveyer means for transporting solid and/or powdered feeds, such, such as a screw conveyer or pneumatic conveyer, and a pump. At least a portion of the conveyer means is heated to a sufficiently high temperature to produce the molten mixture. The molten mixture may optionally be directed to an accumulation tank, before being directed to a pump, which directs the molten mixture to an atomizer. Optionally, an in-line mixer may be used before or after the pump to ensure the molten mixture is substantially homogeneous. In each of these extruders the molten mixture is mixed to form a uniformly mixed extrudate. Such mixing may be accomplished by various mechanical and processing means, including mixing elements, kneading elements, and shear mixing by backflow. Thus, in such devices, the composition is fed to the extruder, which produces a molten mixture that can be directed to the atomizer.

In one embodiment, the composition is fed to the extruder in the form of a solid powder. The powdered feed can be prepared using methods well known in the art for obtaining powdered mixtures with high content uniformity. Generally, it is desirable that the particle sizes of the drug, glyceride, and poloxamer be similar to obtain a substantially uniform blend. However, this is not essential to the successful practice of the invention.

An example of a process for preparing a substantially uniform blend is as follows. First, the glyceride and poloxamer are milled so that their particle sizes are about the same as that of the drug; next, the drug, glyceride, and poloxamer are blended in a V-blender for 20 minutes; the resulting blend is then de-lumped to remove large particles; the resulting blend is finally blended for an additional 4 minutes. In some cases it is difficult to mill the glyceride and poloxamer to the desired particle size since many of these materials tend to be waxy substances and the heat generated during the milling process can gum up the milling equipment. In such cases, small particles of the glyceride and poloxamer can be formed using a melt- or spray-congeal process, as described below. The resulting congealed particles of glyceride and poloxamer can then be blended with the drug to produce the feed for the extruder.

Another method for producing the feed to the extruder is to melt the glyceride and poloxamer in a tank, mix in the drug as described above for the tank system, and then cool the molten mixture, producing a solidified mixture of drug and carrier. This solidified mixture can then be milled to a uniform particle size and fed to the extruder.

A two-feed extruder system can also be used to produce the molten mixture. In this system the drug, glyceride, and poloxamer, all in powdered form, are fed to the extruder through the same or different feed ports. In this way, the need for blending the components is eliminated.

Alternatively, the glyceride and poloxamer in powder form may be fed to the extruder at one point, allowing the extruder to melt the glyceride and poloxamer. The drug is then added to the molten glyceride and poloxamer through a second feed delivery port part way along the length of the extruder, thus minimizing the contact time of the drug with the molten glyceride and poloxamer. The closer the second feed delivery port is to the extruder exit, the lower is the residence time of drug in the extruder. Multiple-feed extruders can be used when optional excipients are included in the multiparticulate.

In another method, the composition is in the form of large solid particles or a solid mass, rather than a powder, when fed to the extruder. For example, a solidified mixture can be prepared as described above and then molded to fit into the cylinder of a ram extruder and used directly without milling.

In another method, the glyceride and poloxamer can be first melted in, for example, a tank, and fed to the extruder in molten form. The drug, typically in powdered form, may then be introduced to the extruder through the same or a different delivery port used to feed the glyceride and poloxamer into the extruder. This system has the advantage of separating the melting step for the glyceride and poloxamer from the mixing step, minimizing contact of the drug with the molten glyceride and poloxamer.

In each of the above methods, the extruder should be designed such that it produces a molten mixture with the drug crystals uniformly distributed in the glyceride/poloxamer mixture. Generally, the temperature of the extrudate should be about 10° C. or more above the temperature at which the drug and carrier mixture becomes fluid. The various zones in the extruder should be heated to appropriate temperatures to obtain the desired extrudate temperature as well as the desired degree of mixing or shear, using procedures well known in the art. As discussed above for mechanical mixing, a minimum shear should be used to produce a uniform molten mixture, such that the crystalline form of the drug is unchanged and that dissolution or formation of amorphous drug is minimized.

The feed is preferably molten prior to congealing for at least 5 seconds, more preferably at least 10 seconds, and most preferably at least 15 seconds, so as to ensure adequate homogeneity of the drug/glyceride/poloxamer melt. It is also preferred that the molten mixture remain molten for no more than about 20 minutes to limit exposure of the drug to the molten mixture. As described above, depending on the reactivity of the chosen glyceride/poloxamer mixture, it may be preferable to further reduce the time that the mixture is molten to well below 20 minutes in order to limit drug degradation to an acceptable level. In such cases, such mixtures may be maintained in the molten state for less than 15 minutes, and in some cases, even less than 10 minutes. When an extruder is used to produce the molten feed, the times above refer to the mean time from when material is introduced to the extruder to when the molten mixture is congealed. Such mean times can be determined by procedures well known in the art. In one exemplary method, a small amount of dye or other similar compound is added to the feed while the extruder is operating under nominal conditions. Congealed multiparticulates are then collected over time and analyzed for the dye, from which the mean time is determined.

When the drug is a crystalline hydrate, it may be desirable to maintain a high water activity in the drug/glyceride/poloxamer admixture to reduce dehydration of the drug. This can be accomplished either by adding water to the powdered feed blend or by injecting water directly into the extruder by metering a controlled amount of water into a separate delivery port. In either case, sufficient water should be added to ensure the water activity is high enough to maintain the desired form of the crystalline drug. Generally, it is desirable to keep the water activity of any material in contact with drug hydrate in the 30% to 100% RH range. This can be accomplished by ensuring that the concentration of water in the molten carrier is 30% to 100% of the solubility of water in the molten glyceride/poloxamer mixture at the maximum process temperature. In some cases, a small excess of water above the 100% water solubility limit may be added to the mixture.

Once the molten mixture has been formed, it is delivered to an atomizer that breaks the molten feed into small droplets. Virtually any method can be used to deliver the molten mixture to the atomizer, including the use of pumps and various types of pneumatic devices (e.g., pressurized vessels, piston pots). When an extruder is used to form the molten mixture, the extruder itself can be used to deliver the molten mixture to the atomizer. Typically, the molten mixture is maintained at an elevated temperature while delivering the mixture to the atomizer to prevent solidification of the mixture and to keep the molten mixture flowing.

Generally, atomization occurs in one of several ways, including (1) by "pressure" or single-fluid nozzles; (2) by two-fluid nozzles; (3) by centrifugal or spinning-disk atomizers, (4) by ultrasonic nozzles; and (5) by mechanical vibrating nozzles. Detailed descriptions of atomization processes can be found in Lefebvre, *Atomization and Sprays* (1989) or in *Perry's Chemical Engineers' Handbook* (7th Ed. 1997). Preferably, a centrifugal or spinning-disk atomizer is used, such as the FX1 100-mm rotary atomizer manufactured by Niro A/S (Soeborg, Denmark).

Once the molten mixture has been atomized, the droplets are congealed, typically by contact with a gas or liquid at a temperature below the solidification temperature of the droplets. Typically, it is desirable that the droplets are congealed in less than about 60 seconds, preferably in less than about 10 seconds, more preferably in less than about 1 second. Often, congealing at ambient temperature results in sufficiently rapid solidification of the droplets. However, the congealing step often occurs in an enclosed space to simplify collection of the multiparticulates. In such cases, the temperature of the congealing media (either gas or liquid) will increase over time as the droplets are introduced into the enclosed space, potentially effecting the formation of the multiparticulates or the chemical stability of the drug. Thus, a cooling gas or liquid is often circulated through the enclosed space to maintain a constant congealing temperature. When it is desirable to minimize the time the drug is exposed to high temperatures, e.g., to prevent degradation, the cooling gas or liquid can be cooled to below ambient temperature to promote rapid congealing, thus minimizing formation of degradants.

Additional details of melt-congeal processes are disclosed in commonly assigned U.S. patent application Ser. Nos. 11/003,856 ("Improved Azithromycin Multiparticulate Dosage Forms by Melt-Congeal Processes," and 11/004,165 ("Extrusion Process for Forming Chemically Stable Drug Multiparticulates," both filed concurrently herewith.

Following formation of the multiparticulates, it may be desired to post-treat the multiparticulates to improve drug crystallinity and/or the stability of the multiparticulate. In one embodiment the multiparticulates comprise a drug, a glyceride, and a poloxamer, the glyceride/poloxamer mixture having a melting point of $T_m$ in ° C.; the multiparticulates are treated after formation by at least one of (i) heating the multiparticulates to a temperature of at least 35° C. and less than ($T_m$° C.-10° C.), and (ii) exposing the multiparticulates to a mobility-enhancing agent. This post-treatment step results in an increase in drug crystallinity in the multiparticulates and typically an improvement in at least one of the chemical stability, physical stability, and dissolution stability of the multiparticulates. Post-treatment processes are disclosed more fully in commonly assigned U.S. patent application Ser. No. 11/003,664, ("Multiparticulate Compositions with Improved Stability," filed concurrently herewith.

The multiparticulates may also be mixed or blended with one or more pharmaceutically acceptable materials to form a suitable dosage form. Suitable dosage forms include tablets, capsules, sachets, oral powders for constitution, and the like.

Other features and embodiments of the invention will become apparent from the following examples, which are given for illustration of the invention, rather than for limiting its intended scope.

EXAMPLE 1

Multiparticulates were made comprising 50 wt % azithromycin dihydrate, 40 wt % of the glyceride COMPRITOL 888 ATO and 10 wt % poloxamer 407 (of a block copolymer of ethylene and propylene oxides commercially available as PLURONIC F127 or LUTROL F127 from BASF, Mt. Olive, N.J.). First, 250 g crystalline azithromycin dihydrate, 200 g of the COMPRITOL 888 ATO and 50 g of the PLURONIC F127 were blended in a twinshell blender for 20 minutes. This blend was then de-lumped using a Fitzpatrick L1A mill at 3000 rpm, knives forward using a 0.0065-inch screen. The mixture was blended again in a twinshell blender for 20 minutes, forming a preblend feed.

The preblend feed was delivered to a B&P 19-mm twin-screw extruder (MP19-TC with a 25 L/D ratio purchased from B & P Process Equipment and Systems, LLC, Saginaw, Mich.) at a rate of 130 g/min, producing a molten feed suspension of the azithromycin dihydrate in the glyceride/poloxamer carrier at a temperature of about 90° C. The feed suspension was then delivered to the center of a spinning-disk atomizer.

The spinning disk atomizer, which was custom made, consists of a bowel-shaped stainless steel disk of 10.1 cm (4 inches) in diameter. The surface of the disk is heated with a thin film heater beneath the disk to about 90° C. That disk is mounted on a motor that drives the disk of up to approximately 10,000 RPM. The entire assembly is enclosed in a plastic bag of approximately 8 feet in diameter to allow congealing and to capture microparticulates formed by the atomizer. Air is introduced from a port underneath the disk to provide cooling of the multiparticulates upon congealing and to inflate the bag to its extended size and shape.

A suitable commercial equivalent, to this spinning disk atomizer, is the FX1 100-mm rotary atomizer manufactured by Niro A/S (Soeborg, Denmark).

The surface of the spinning disk atomizer was maintained at 90° C., and the disk was rotated at 5500 rpm, while forming the azithromycin multiparticulates. The mean residence time of the azithromycin in the extruder was about 60 seconds and the total time the azithromycin was in the molten suspension was less than about 3 minutes. The particles formed by the spinning-disk atomizer were congealed in ambient air and collected. The azithromycin multiparticulates, prepared by this method, had a diameter of about 200 μm.

The properties of the melt-congealed microspheres such as particle size can be controlled by the viscosity of the melt and processing conditions. Given the combination of the materials in the preferred embodiments in the present invention, the viscosity of the melt is unchanged as long as the temperature of the heating system is kept at 90° C. The size of azithromycin multiparticulates can be controlled by the feed rate to the disk (the amount of molten materials fed into the spinning disk atomizer) and the disk speed. For example, particles with a diameter of about 200 μm can be formed by a combination of (1) feed rate at 8.4 kg/hr and disk speed at 5500 RPM or (2) feed rate at 20 kg/hr and disk speed at 5800 RPM, or (3) feed rate at 25 kg/hr and disk speed at 7100 RPM.

The so-made multiparticulates were annealed by placing samples of them in a shallow tray at a depth of about 2 cm and the tray was then placed in a controlled atmosphere oven at 47° C. and 70% RH for 24 hours. PXRD analysis of the multiparticulates showed that 85 wt % of the azithromycin present was still crystalline dihydrate, confirming the presence of two phases in the multiparticulates.

EXAMPLES 2-6

Azithromycin-containing multiparticulates were made as in Example 1, with the processing variables noted in Table 1. The ratio of ingredients was varied to determine the effect on azithromycin release. PXRD analysis confirmed that >90 wt % of the azithromycin in the multiparticulates was crystalline dihydrate.

TABLE 1

| Ex. No. | Formulation (Azithromycin/ COMPRITOL 888 ATO/PLURONIC F127, wt %) | Feed Rate (g/min) | Disk speed (rpm) | Disk Temp (° C.) | Batch size (g) | Annealing (° C./% RH; days) |
|---|---|---|---|---|---|---|
| 1 | 50/40/10 | 130 | 5500 | 90 | 500 | 47/70; 1 |
| 2 | 50/45/5 | 140 | 5500 | 90 | 491 | 47/70; 1 |
| 3 | 50/46/4 | 140 | 5500 | 90 | 4968 | 40/75; 5 |
| 4 | 50/47/3 3.45 wt % H$_2$O added to preblend feed | 180 | 5500 | 86 | 1015 | 40/75; 5 |
| 5 | 50/48/2 | 130 | 5500 | 90 | 500 | 47/70; 1 |
| 6 | 50/50/0 | 130 | 5500 | 90 | 500 | 47/70; 1 |

The rate of release of azithromycin from the multiparticulates of Examples 1-6 was determined using the following procedure. A sample of the multiparticulates was placed into a USP Type 2 dissoette flask equipped with TEFLON®-coated paddles rotating at 50 rpm. For Examples 1-3 and 6, 1060 mg of multiparticulates were added to the dissolution medium; for Example 4, 1048 mg were added; for Example 5, 1000 mg were added. The flask contained 1000 mL of 50 mM KH$_2$PO$_4$ buffer, pH 6.8, held at 37.0±0.5° C. The multiparticulates were pre-wet with 10 mL of the buffer before being added to the flask. A 3-mL sample of the fluid in the flask was then collected at 5, 15, 30, 60, 120, and 180 minutes following addition of the multiparticulates to the flask. The samples were filtered using a 0.45-μm syringe filter prior to analyzing via HPLC (Hewlett Packard 1100, Waters Symmetry C$_8$ column, 45:30:25 acetonitrile:methanol:25 mM KH$_2$PO$_4$ buffer at 1.0 mL/min, absorbance measured at 210 nm with a diode array spectrophotometer). The results of these dissolution tests are given in Table 2.

TABLE 2

| Example No. | Time (min) | Azithromycin Released (%) |
|---|---|---|
| 1 | 0 | 0 |
|   | 5 | 32 |
|   | 15 | 67 |
|   | 30 | 90 |
|   | 60 | 99 |
|   | 120 | 99 |
|   | 180 | 100 |
| 2 | 0 | 0 |
|   | 15 | 28 |
|   | 30 | 46 |
|   | 60 | 69 |
|   | 120 | 87 |
|   | 180 | 90 |
| 3 | 0 | 0 |
|   | 15 | 25 |
|   | 30 | 42 |
|   | 60 | 64 |
|   | 120 | 86 |
|   | 180 | 93 |
| 4 | 0 | 0 |
|   | 15 | 14 |
|   | 30 | 27 |
|   | 60 | 44 |
|   | 120 | 68 |
|   | 180 | 81 |
| 5 | 0 | 0 |
|   | 5 | 3 |
|   | 15 | 11 |
|   | 30 | 23 |
|   | 60 | 41 |
|   | 120 | 66 |
|   | 180 | 81 |
| 6 | 0 | 0 |
|   | 5 | 4 |
|   | 15 | 10 |
|   | 30 | 19 |
|   | 60 | 32 |
|   | 120 | 50 |
|   | 180 | 62 |

The dissolution rate constant k in units of min$^{-1}$ for the multiparticulates of Examples 1-6 were calculated by fitting the data to the above-noted equation I and solving for k:

$$A_t = A_\infty \cdot [1 - e^{-kt}]$$

where $A_t$ is the percentage of azithromycin released from the multiparticulates at time t, $A_\infty$ is the percentage of azithromycin released from the multiparticulates over a long period of time (equal to the amount released at 180 minutes plus the amount remaining in the multiparticulates after the test) and t is the time in minutes. The so-calculated dissolution rate constants (k) and the time required for half of the drug to be released ($t_{1/2}$) for the multiparticulates of Examples 1-6 are given in Table 3.

TABLE 3

| Ex. No. | Formulation (Azithromycin/ COMPRITOL 888 ATO/ PLURONIC F127, wt %) | Poloxamer to Glyceride Ratio | % Drug Released at 30 min. | % Drug Released at 60 min. | k (1/min) | $t_{1/2}$ (min) |
|---|---|---|---|---|---|---|
| 1 | 50/40/10 | 0.25 | 90 | 99 | 0.077 | 8 |
| 2 | 50/45/5 | 0.11 | 46 | 69 | 0.019 | 33 |
| 3 | 50/46/4 | 0.09 | 42 | 64 | 0.017 | 37 |
| 4 | 50/47/3 | 0.06 | 27 | 44 | 0.010 | 63 |
| 5 | 50/48/2 | 0.04 | 23 | 41 | 0.009 | 70 |
| 6 | 50/50/0 | 0.00 | 19 | 32 | 0.006 | 105 |

The results in Table 3 show that as the concentration of the poloxamer in the multiparticulates is decreased (and the ratio of poloxamer to glyceride is decreased), the dissolution rate constant decreases, as does the amount of drug released at 30 min and 60 min, while $t_{1/2}$ increases with decreasing poloxamer to glyceride ratio.

EXAMPLE 7

Multiparticulates were made as in Example 1 comprising azithromycin dihydrate, the glyceride STEROTEX NF and the poloxamer PLURONIC F127 with the processing variables noted in Table 4. PXRD analysis of the multiparticulates confirmed that >90 wt % of the drug present was crystalline.

TABLE 4

| Formulation (Azithromycin/ STEROTEX/ PLURONIC F127, wt %) | Feed Rate (g/min) | Disk speed (rpm) | Disk Temp (° C.) | Batch size (g) | Annealing (° C./% RH; days) |
|---|---|---|---|---|---|
| 50/46/4 | 140 | 5500 | 85 | 719 | 40/75; 5 |

The so-made multiparticulates were evaluated in the same manner as those of Examples 1-6, with a sample size of 1060 mg. The results of this dissolution test are given in Table 5.

TABLE 5

| Time (min) | Azithromycin Released (%) |
|---|---|
| 0 | 0 |
| 15 | 22 |
| 30 | 36 |
| 60 | 52 |
| 120 | 68 |
| 180 | 74 |

From the data in Table 5, the dissolution rate constant k was calculated as noted above and is given in Table 6. The dissolution rate constant for Example 3 is shown again for comparison.

TABLE 6

| Example No. | Formulation (Azithromycin/ Glyceride/ PLURONIC F127, wt %) | % Drug Released at 30 min. | % Drug Released at 60 min. | k (1/min) | $t_{1/2}$ (min) |
|---|---|---|---|---|---|
| 7 (with STEROTEX) | 50/46/4 | 36 | 52 | 0.011 | 57 |
| 3 | 50/46/4 | 42 | 64 | 0.017 | 37 |

TABLE 6-continued

| Example No. | Formulation (Azithromycin/ Glyceride/ PLURONIC F127, wt %) | % Drug Released at 30 min. | % Drug Released at 60 min. | k (1/min) | $t_{1/2}$ (min) |
|---|---|---|---|---|---|
| (with COMPRITOL 888 ATO) | | | | | |

The results in Table 6 show that the dissolution rate constant decreases for multiparticulates containing STEROTEX NF, compared to multiparticulates containing COMPRITOL 888 ATO.

EXAMPLE 8

Multiparticulates were made comprising 50 wt % azithromycin dihydrate, 47 wt % COMPRITOL 888 ATO, and 3 wt % LUTROL F127 using the following procedure. First, 140 kg azithromycin dihydrate was weighed and passed through a Quadro Comil 196S with a speed of 900 rpm, and equipped with a No. 2C-075-H050/60 screen (special round, 0.075"), a No. 2F-1607-254 impeller, and a 0.225 inch spacer between the impeller and screen. Next, 8.4 kg of the LUTROL F127 and then 131.6 kg of the COMPRITOL 888 ATO were weighed and passed through a Quadro 194S Comil set at 650 rpm and equipped with a No. 2C-075-R03751 screen (0.075"), a No. 2C-1601-001 impeller, and a 0.225-inch spacer between the impeller and screen. This mixture was blended using a Gallay 38 cubic foot stainless-steel bin blender rotating at 10 rpm for 40 minutes, for a total of 400 rotations, forming a preblend feed.

The preblend feed was delivered to a Leistritz 50 mm twin-screw extruder (Model ZSE 50, American Leistritz Extruder Corporation, Somerville, N.J.) at a rate of about 20 kg/hr. The extruder was operated in co-rotating mode at about 100 rpm, and interfaced with a melt/spray-congeal unit. The extruder had five segmented barrel zones and an overall extruder length of 20 screw diameters (1.0 m). Water was injected into barrel number 2 at a rate of 6.7 g/min (2 wt %). The extruder's rate of extrusion was adjusted so as to produce a molten feed suspension of the azithromycin dihydrate in the COMPRITOL 888 ATO/LUTROL F127 at a temperature of about 90° C.

The feed suspension was delivered to the spinning-disk atomizer of Example 1, rotating at 6400 rpm. The maximum total time the azithromycin was exposed to the molten suspension was less than 10 minutes. The particles formed by the spinning-disk atomizer were cooled and congealed in the presence of cooling air circulated through the product collection chamber. The mean particle size was determined to be about 200 μm using a Malvern particle size analyzer.

The so-formed multiparticulates were post-treated by placing a sample in a sealed barrel that was then placed in a controlled atmosphere chamber at 40° C. for 10 days. Samples of the post-treated multiparticulates were evaluated by PXRD, which showed that about 99% of the azithromycin in the multiparticulates was in the crystalline dihydrate form.

To determine the dissolution rate of these multiparticulates, a sample of the multiparticulates containing about 2000 mgA of azithromycin was placed into a 125-mL bottle, along with 19.36 g sucrose, 352 mg trisodium phosphate, 250 mg magnesium hydroxide, 67 mg hydroxypropyl cellulose, 67 mg xanthan gum, 110 mg colloidal silicon dioxide, 400 mg titanium dioxide, 140 mg cherry flavoring and 230 mg banana flavoring. Next, 60 mL of purified water was added, and the bottle was shaken for 30 seconds. The contents were added to a USP Type 2 dissoette flask equipped with TEFLON®-coated paddles rotating at 50 rpm. The flask contained 840 mL of a buffered test solution comprising 100 mM $Na_2HPO_4$ buffer, pH 6.0, maintained at 37.0±0.5° C. The bottle was rinsed twice with 20 mL of the buffer from the flask, and the rinse was returned to the flask to make up a 900 mL final volume. A 3 mL sample of the fluid in the flask was then collected at 15, 30, 60, 120, and 180 minutes following addition of the multiparticulates to the flask. The samples were filtered using a 0.45-μm syringe filter prior to analyzing via HPLC (Hewlett Packard 1100, Waters Symmetry $C_8$ column, 45:30:25 acetonitrile:methanol:25 mM $KH_2PO_4$ buffer at 1.0 mL/min, absorbance measured at 210 nm with a diode array spectrophotometer). The results of these dissolution tests are given in Table 7.

TABLE 7

| Example | Test Medium | Time (min) | Azithromycin Released (mg) | Azithromycin Released (%) |
|---|---|---|---|---|
| 8 | 100 mM $Na_2HPO_4$ buffer, pH 6.0, | 0 | 0 | 0 |
| | | 15 | 720 | 36 |
| | | 30 | 1140 | 57 |
| | | 60 | 1620 | 81 |
| | | 120 | 1900 | 95 |
| | | 180 | 1960 | 98 |

From the data in Table 7, the dissolution rate constant k was calculated as noted above and is given in Table 8.

TABLE 8

| Example No. | Formulation (Azithromycin/ COMPRITOL 888 ATO/ LUTROL F127, wt %) | % Drug Released at 30 min. | % Drug Released at 60 min. | k (1/min) | $t_{1/2}$ (min) |
|---|---|---|---|---|---|
| 8 | 50/47/3* | 57 | 81 | 0.029 | 24 |

*2 wt % water added to extruder.

EXAMPLES 9-11

Multiparticulates were prepared comprising the drug amlodipine, the glyceride COMPRITOL 888 ATO and the poloxamer PLURONIC F127. For Example 9, the multiparticulates comprised 10 wt % amlodipine, 60 wt % of the COMPRITOL 888 ATO and 30 wt % of the PLURONIC F127. For Example 10, the multiparticulates comprised 10 wt % amlodipine, 70 wt % of the COMPRITOL 888 ATO and 20 wt % of the PLURONIC F127. For Example 11, the multiparticulates comprised 10 wt % amlodipine, 80 wt % of the COMPRITOL 888 ATO and 10 wt % of the PLURONIC F127. In each case, PXRD analysis of the multiparticulates confirmed that >90 wt % of the drug present was crystalline.

The multiparticulates were prepared using the following melt-congeal procedure. First, the COMPRITOL 888 ATO and the PLURONIC F127 were added to a sealed, jacketed stainless-steel tank equipped with a mechanical mixing paddle. Heating fluid at 92° C. was circulated through the jacket of the tank. After about 25 minutes, the mixture had melted, having a temperature of about 90° C. This mixture was then mixed at 700 rpm for 5 minutes. Next, amlodipine that had been pre-heated to 90° C. at ambient RH was added to the melt and mixed at a speed of 700 rpm for 5 minutes, resulting in a feed suspension of the amlodipine in the molten components.

Using a gear pump, the feed suspension was then pumped at a rate of 140 g/min to the center of the spinning-disk atomizer of Example 1, the surface of which was heated to 90° C. The disk was spinning at 7000 rpm for Examples 8-9 and at 10,000 rpm for Example 10. The particles formed by the spinning-disk atomizer were congealed in ambient air and collected. Table 9 summarizes the processing variables.

TABLE 9

| Ex. No. | Formulation (Amlodipine/ COMPRITOL 888 ATO/ PLURONIC F127, wt %) | Melt time (min) | Stir rate (rpm) | Stir time (min) | Feed Rate (g/min) | Disk speed (rpm) | Disk Temp (° C.) | Batch size (g) |
|---|---|---|---|---|---|---|---|---|
| 9 | 10/60/30 | 25 | 700 | 5 | 140 | 7000 | 91 | 25 |
| 10 | 10/70/20 | 25 | 700 | 5 | 140 | 7000 | 90 | 25 |
| 11 | 10/80/10 | 20 | 700 | 5 | 140 | 10000 | 90 | 20 |

The rate of release of amlodipine from the multiparticulates of Examples 9-11 was determined using the following procedure. A 5.5 mg sample of the multiparticulates was placed into a USP Type 2 dissoette flask equipped with TEFLON®-coated paddles rotating at 75 rpm. The flask contained 500 mL of 0.022 M sodium acetate (pH 4.5) buffer held at 37.0±0.5° C. The multiparticulates were pre-wet with 15 mL of the buffer before being added to the flask. A 3-mL sample of the fluid in the flask was then collected at 5, 15, 30, 45, and 60 minutes following addition of the multiparticulates to the flask. The samples were filtered using a 0.45-μm syringe filter prior to analyzing via HPLC (Hewlett Packard 1100, Waters Norapak $C_{18}$ column, 50 mM triethylamine orthophosphate at 1.0 mL/min, absorbance measured at 237 nm with a diode array spectrophotometer). The results of these dissolution tests are given in Table 10.

TABLE 10

| Example No. | Time (min) | Amlodipine Released (%) |
|---|---|---|
| 9 | 0 | 0 |
|  | 5 | 94 |
|  | 15 | 97 |
|  | 30 | 97 |
|  | 45 | 97 |
|  | 60 | 97 |
| 10 | 0 | 0 |
|  | 5 | 88 |
|  | 15 | 94 |
|  | 30 | 96 |
|  | 45 | 96 |
|  | 60 | 97 |
| 11 | 0 | 0 |
|  | 5 | 9 |
|  | 15 | 22 |
|  | 30 | 29 |
|  | 45 | 35 |
|  | 60 | 41 |

From the data in Table 10, the dissolution rate constants k were calculated as noted above and are given in Table 11.

TABLE 11

| Ex. No. | Formulation (Amlodipine/ COMPRITOL 888 ATO/ PLURONIC F127, wt %) | % Drug Released at 30 min. | % Drug Released at 60 min. | k (1/min) | $t_{1/2}$ (min) |
|---|---|---|---|---|---|
| 9 | 10/60/30 | 97 | 97 | 0.597 | 1.1 |
| 10 | 10/70/20 | 96 | 97 | 0.436 | 1.4 |
| 11 | 10/80/10 | 29 | 41 | 0.010 | 63 |

The results in Table 11 show that as the concentration of the poloxamer in the multiparticulates is decreased, the dissolution rate constant decreases.

EXAMPLES 12-14

Multiparticulates were prepared as in Examples 9-11 comprising the drug cetirizine, the glyceride COMPRITOL 888 ATO and the poloxamer PLURONIC F127 in various ratios to determine the effect on cetirizine release, with the processing variables noted in Table 12. In each case, PXRD analysis of the multiparticulates confirmed that >70 wt % of the drug present was crystalline.

TABLE 12

| Ex. No. | Formulation (Cetirizine/ COMPRITOL 888 ATO/PLURONIC F127, wt %) | Stir time (min) | Feed Rate (g/min) | Disk Speed (rpm) | Disk Temp (° C.) | Batch size (g) |
|---|---|---|---|---|---|---|
| 12 | 40/60/0 | 5 | 140 | 5500 | 90 | 20 |
| 13 | 40/55/5 | 5 | 140 | 5500 | 90 | 20 |
| 14 | 40/50/10 | 5 | 140 | 10,000 | 92 | 20 |

The rate of release of cetirizine from the multiparticulates of Examples 12-14 was determined using the following procedure. A 10 mg sample of the multiparticulates was placed into 150 mL of stirring deionized water in a flask. A 1-mL sample of the fluid in the flask was then collected at 1, 2, 3, 4, 5, 8, 13, 15, and 25 minutes following addition of the multiparticulates to the flask. The absorbance at 231 nm was measured using a UV-VIS spectrophotometer. The results of these dissolution tests are given in Table 13.

TABLE 13

| Example No. | Time (min) | Cetirizine Released (%) |
|---|---|---|
| 12 | 0 | 0 |
|  | 1 | 10 |
|  | 2 | 19 |
|  | 3 | 27 |
|  | 4 | 35 |
|  | 5 | 41 |
|  | 8 | 57 |
|  | 12 | 72 |
|  | 14 | 77 |
|  | 25 | 92 |
| 13 | 0 | 0 |
|  | 1 | 11 |
|  | 2 | 22 |
|  | 3 | 31 |
|  | 4 | 38 |
|  | 5 | 45 |
|  | 8 | 62 |
|  | 12 | 76 |
|  | 14 | 80 |
|  | 26 | 93 |
| 14 | 0 | 0 |
|  | 1 | 61 |
|  | 2 | 84 |
|  | 3 | 94 |
|  | 4 | 97 |
|  | 5 | 99 |
|  | 8 | 100 |
|  | 13 | 100 |
|  | 15 | 100 |

From the data in Table 13, the dissolution rate constants were calculated as noted above and are given in Table 14.

TABLE 14

| Ex. No. | Formulation (Cetirizine/ COMPRITOL 888 ATO/PLURONIC F127, wt %) | k (1/min) | $t_{1/2}$ (min) |
|---|---|---|---|
| 12 | 40/60/0 | 0.597 | 5.9 |
| 13 | 40/55/5 | 0.436 | 5.2 |
| 14 | 40/50/10 | 0.010 | 0.66 |

The results in Table 14 show that as the concentration of the poloxamer in the multiparticulates is increased, the dissolution rate constants increase.

The terms and descriptions which have been employed in the foregoing specification are used therein as terms of description and not of limitation, and there is no intention, in the use of such terms and expressions, of excluding equivalents of the features shown and described or portions thereof, it being recognized that the scope of the invention is defined and limited by the claims which follow.

We claim:

1. A pharmaceutical composition providing controlled release of azithromycin, comprising a plurality of multiparticulates, said multiparticulates comprising said azithromycin wherein at least 70 wt % of said azithromycin is crystalline, a poloxamer and a glyceride having at least one alkylate substituent of at least 16 carbon atoms, wherein the weight ratio of poloxamer to glyceride ranges from about 0.01 to 0.50, and wherein said multiparticulates comprise crystalline azithromycin suspended in a mixture of said glyceride and poloxamer.

2. The composition of claim 1 wherein said azithromycin is azithromycin dihydrate.

3. The composition of claim 1 or claim 2 wherein at least 80 wt % of said azithromycin is crystalline.

4. The composition of claim 1 or claim 2 wherein said alkylate substituent is selected from the group consisting of palmitate, stearate, oleate, linoleate, arachidate, behenate, lignocerate, ricinoleate and mixtures thereof.

5. The composition of claim 1 or claim 2 wherein said glyceride is selected from the group consisting of: mixtures of glyceryl mono-, di-, and tribehenates; mixtures of glyceryl tripalmitate and glyceryl tristearate; glyceryl tri-behenates; and mixtures thereof.

6. The composition of claim 1 or claim 2 wherein said poloxamer is selected from the group consisting of poloxamer 188, poloxamer 237, poloxamer 338, poloxamer 407 and mixtures thereof.

7. The composition of claim 1 or claim 2 wherein said poloxamer has a molecular weight of at least 4,700 daltons.

8. The composition of claim 1 or claim 2 wherein said poloxamer is solid at ambient temperatures.

9. The composition of claim 1 or claim 2 wherein said poloxamer is homogeneously distributed throughout said glyceride.

10. A process for forming multiparticulates, comprising:
   (a) forming a molten mixture comprising azithromycin, a poloxamer and a glyceride having at least one alkylate substituent of at least 16 carbon atoms, wherein said molten mixture has a viscosity less than about 20,000 cp and comprises crystalline azithromycin suspended in a mixture of said glyceride and poloxamer;
   (b) forming droplets from said molten mixture; and
   (c) solidifying said droplets to form multiparticulates
   wherein at least 70 wt % of said azithromycin in said multiparticulates is crystalline, and
   wherein the ratio of poloxamer to glyceride ranges from about 0.01 to 0.50.

11. The process of claim 10 wherein said azithromycin is azithromycin dihydrate.

12. The process of claim 10 or claim 11 wherein at least 80 wt % of said azithromycin in said multiparticulate is crystalline.

13. The process of claim 10 or claim 11 wherein said molten mixture has a viscosity of less than about 10,000 cp.

14. A method for controlling the release rate of azithromycin from a multiparticulate, comprising:
   (a) determining a desired release rate of said azithromycin from said multiparticulate;
   (b) forming multiparticulates comprising
      (1) forming a molten mixture comprising crystalline azithromycin suspended in a mixture of a poloxamer and a glyceride having at least one alkylate substituent of at least 16 carbon atoms;
      (2) forming droplets from said molten mixture; and
      (3) solidifying said droplets to form multiparticulates wherein at least 70 wt % of said azithromycin in said multiparticulates is crystalline; and
   (c) prior to (b) selecting a weight ratio of said poloxamer to said glyceride to achieve said desired release rate, wherein the weight ratio of poloxamer to glyceride ranges from about 0.01 to 0.50.

15. The method of claim 14 wherein said glyceride comprises at least 20 wt % of said multiparticulate.

* * * * *